(12) United States Patent
Remus et al.

(10) Patent No.: US 12,325,576 B2
(45) Date of Patent: Jun. 10, 2025

(54) SEALED ABSORBENT ARTICLE PACKAGE WITH NATURAL FIBERS

(71) Applicant: The Procter & Gamble Company, Cincinnati, OH (US)

(72) Inventors: Michael Remus, Schwlbach am Taunus (DE); Stephan Spiekers, Crailsheim (DE); Peter Kramkowski, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 238 days.

(21) Appl. No.: 17/875,454

(22) Filed: Jul. 28, 2022

(65) Prior Publication Data

US 2023/0048153 A1 Feb. 16, 2023

Related U.S. Application Data

(60) Provisional application No. 63/227,354, filed on Jul. 30, 2021.

(51) Int. Cl.
*A61F 13/551* (2006.01)
*B65D 85/18* (2006.01)

(52) U.S. Cl.
CPC ........ *B65D 85/18* (2013.01); *A61F 13/55115* (2013.01); *A61F 13/55145* (2013.01)

(58) Field of Classification Search
CPC .... B65D 85/18; B65D 75/5827; B65D 85/07; A61F 13/55115; A61F 13/55145; A61F 13/551; A61F 13/5514
See application file for complete search history.

(56) References Cited

U.S. PATENT DOCUMENTS 2,146,308 A  2/1939  Maxfield
2,290,564 A  7/1942  Krueger
(Continued)

FOREIGN PATENT DOCUMENTS

EP  0439209 A1  7/1991
EP  0450114 A1  10/1991
(Continued)

OTHER PUBLICATIONS

Jonathan Fowle et al. "Paper-based flexible packaging", 2003, pp. 91-123.
(Continued)

*Primary Examiner* — Orlando E Aviles
*Assistant Examiner* — Jenine Pagan
(74) *Attorney, Agent, or Firm* — Amanda Herman Berghauer

(57) ABSTRACT

A package of one or more absorbent articles, wherein the one or more absorbent articles are sealed within the package is described. The package has a plurality of panels and a top fold line. The plurality of panels includes a consumer-facing panel and a top panel disposed superjacent to the consumer-facing panel. Each of the plurality of panels has an inner surface and an outer surface. The top fold line is disposed between the consumer-facing panel and the top panel, and the top fold line is colinear, at least in part, with a cross-wise crease. And the package material has natural fibers and has a basis weight of between 60 gsm to 120 gsm, more (Continued)

preferably between 65 gsm to 105 gsm, or most preferably between 70 gsm to 90 gsm, as determined via ISO 536 as modified herein.

19 Claims, 23 Drawing Sheets

(56) References Cited

U.S. PATENT DOCUMENTS

| | | | |
|---|---|---|---|
| 2,821,337 A | | 1/1958 | Morgan, Jr. |
| 3,312,339 A | | 4/1967 | Million |
| 3,462,026 A | | 8/1969 | Maccherone |
| 3,519,197 A | | 7/1970 | Campbell |
| 3,640,450 A | | 2/1972 | Lieberman |
| 3,741,778 A | | 6/1973 | Rowe |
| 3,979,049 A | | 9/1976 | Achelpohl |
| 4,691,368 A | | 9/1987 | Roessiger |
| 4,951,824 A | * | 8/1990 | Kuchenbecker ..... B65D 5/5435 |
| | | | 229/207 |
| 4,988,332 A | | 1/1991 | Mattle |
| 5,065,868 A | | 11/1991 | Cornelissen |
| 5,312,659 A | * | 5/1994 | Otsuka ................. B65D 31/02 |
| | | | 428/458 |
| 5,457,944 A | | 10/1995 | Lipes |
| 5,468,206 A | | 11/1995 | Buchanan |
| 5,509,915 A | | 4/1996 | Hanson |
| 5,524,756 A | * | 6/1996 | Sutherland ............ B65D 71/16 |
| | | | 206/427 |
| 5,830,118 A | | 11/1998 | Nicholson |
| 5,908,113 A | | 6/1999 | Takemasa et al. |
| 5,934,470 A | | 8/1999 | Bauer et al. |
| 6,026,957 A | | 2/2000 | Bauer et al. |
| 6,033,112 A | | 3/2000 | Sorenson et al. |
| 6,229,061 B1 | | 5/2001 | Dragoo |
| 6,446,796 B1 | | 9/2002 | Schmidt |
| 6,698,928 B2 | | 3/2004 | Miller |
| 7,004,320 B1 | | 2/2006 | Schmidt et al. |
| 7,721,887 B2 | | 5/2010 | Hancock-cooke et al. |
| 7,780,353 B2 | | 8/2010 | Yoffe |
| 8,074,801 B2 | | 12/2011 | Slayton et al. |
| 8,097,313 B2 | | 1/2012 | Wallat |
| 8,240,915 B2 | | 8/2012 | Sargin et al. |
| 8,348,916 B2 | | 1/2013 | Fujikawa et al. |
| 8,631,939 B2 | | 1/2014 | Benson et al. |
| 8,794,443 B2 | | 8/2014 | Ueda |
| 8,899,418 B2 | | 12/2014 | Francis |
| 9,382,043 B2 | | 7/2016 | Rummo |
| 9,468,566 B2 | | 10/2016 | Rosati et al. |
| 9,827,150 B1 | * | 11/2017 | Sheehan ................ B65D 85/07 |
| 9,878,839 B2 | | 1/2018 | Santos |
| 9,914,562 B2 | | 3/2018 | Fox et al. |
| 9,932,149 B2 | | 4/2018 | Puccini |
| 9,994,376 B2 | | 6/2018 | De Soto-burt et al. |
| 10,378,152 B2 | | 8/2019 | Kinast |
| 10,760,219 B2 | | 9/2020 | Niemi |
| 10,786,404 B2 | | 9/2020 | Cheng et al. |
| 11,396,170 B2 | | 7/2022 | Knauf et al. |
| 11,420,784 B2 | | 8/2022 | Parker et al. |
| 11,794,976 B2 | | 10/2023 | Remus |
| 11,833,019 B2 | * | 12/2023 | Remus ................... B65D 85/07 |
| 2001/0056270 A1 | | 12/2001 | Mizutani et al. |
| 2002/0148749 A1 | | 10/2002 | Briseboi et al. |
| 2003/0106825 A1 | | 6/2003 | Molina et al. |
| 2004/0232024 A1 | | 11/2004 | Guerreschi |
| 2004/0238393 A1 | | 12/2004 | Ohi et al. |
| 2004/0241359 A1 | | 12/2004 | Miksic et al. |
| 2006/0051603 A1 | | 3/2006 | Cleveland et al. |
| 2006/0191985 A1 | | 8/2006 | Norcom |
| 2007/0099542 A1 | | 5/2007 | Sakaguchi et al. |
| 2007/0230834 A1 | | 10/2007 | Schneider |
| 2008/0202965 A1 | * | 8/2008 | DuVal ................... B65D 71/00 |
| | | | 206/394 |
| 2009/0084698 A1 | | 4/2009 | Ito et al. |
| 2009/0145792 A1 | | 6/2009 | Lewis |
| 2009/0157033 A1 | | 6/2009 | Toro et al. |
| 2009/0249751 A1 | | 10/2009 | Hyttel et al. |
| 2010/0150479 A1 | | 6/2010 | Smith |
| 2010/0273377 A1 | | 10/2010 | Files et al. |
| 2011/0046591 A1 | | 2/2011 | Warner |
| 2011/0257616 A1 | | 10/2011 | Lakso et al. |
| 2012/0288693 A1 | | 11/2012 | Stanley et al. |
| 2013/0046271 A1 | | 2/2013 | Pittet et al. |
| 2013/0156352 A1 | | 6/2013 | Koehn |
| 2013/0220860 A1 | | 8/2013 | Bacon |
| 2014/0224391 A1 | * | 8/2014 | Muxlow ................ B65H 37/06 |
| | | | 493/405 |
| 2014/0319003 A1 | | 10/2014 | Hawighorst et al. |
| 2014/0348445 A1 | | 11/2014 | Siesto Casanova et al. |
| 2015/0266663 A1 | | 9/2015 | Joseph |
| 2016/0038628 A1 | | 2/2016 | Klofta et al. |
| 2017/0057721 A1 | | 3/2017 | Lee et al. |
| 2017/0105889 A1 | * | 4/2017 | Nishimura ............. B65D 85/07 |
| 2017/0260694 A1 | | 9/2017 | Torniainen et al. |
| 2017/0274613 A1 | | 9/2017 | Stafford, III |
| 2017/0350074 A1 | | 12/2017 | Kinast |
| 2018/0187377 A1 | | 7/2018 | Ziegenbein |
| 2018/0228675 A1 | * | 8/2018 | Hou .................. A61F 13/55105 |
| 2018/0289564 A1 | | 10/2018 | Sheehan |
| 2018/0304607 A1 | * | 10/2018 | Öhman ................... B32B 15/12 |
| 2018/0334292 A1 | | 11/2018 | Tan |
| 2019/0091077 A1 | | 3/2019 | Cheng et al. |
| 2019/0126603 A1 | | 5/2019 | Zerial |
| 2020/0030162 A1 | | 1/2020 | Lindner et al. |
| 2020/0231365 A1 | | 7/2020 | Veiseh |
| 2020/0354129 A1 | | 11/2020 | Sheehan et al. |
| 2021/0043023 A1 | | 2/2021 | Coder et al. |
| 2021/0108371 A1 | | 4/2021 | Oshima et al. |
| 2021/0114789 A1 | | 4/2021 | Kuiper et al. |
| 2021/0221544 A1 | | 7/2021 | Wallenius et al. |
| 2022/0031531 A1 | | 2/2022 | Remus et al. |
| 2022/0031532 A1 | | 2/2022 | Remus et al. |
| 2022/0031533 A1 | | 2/2022 | Remus et al. |
| 2022/0033159 A1 | | 2/2022 | Remus et al. |
| 2022/0079819 A1 | | 3/2022 | Houben et al. |
| 2022/0110801 A1 | | 4/2022 | Remus et al. |
| 2022/0110802 A1 | | 4/2022 | Remus et al. |
| 2022/0204234 A1 | | 6/2022 | Chapjian |
| 2022/0266563 A1 | | 8/2022 | Schlarp et al. |
| 2022/0362073 A1 | | 11/2022 | Shimizu et al. |

FOREIGN PATENT DOCUMENTS

| | | |
|---|---|---|
| EP | 1291290 A1 | 3/2003 |
| EP | 1618860 A1 | 1/2006 |
| EP | 2276673 B1 | 1/2014 |
| EP | 2730698 A1 | 5/2014 |
| EP | 2796384 A1 | 10/2014 |
| EP | 2704963 B1 | 9/2016 |
| EP | 3561178 A1 | 10/2019 |
| EP | 3575233 B1 | 3/2021 |
| EP | 3643634 B1 | 7/2021 |
| EP | 3865421 A1 | 8/2021 |
| EP | 3954535 A1 | 2/2022 |
| EP | 3901054 B1 | 8/2022 |
| EP | 4070929 A1 | 10/2022 |
| GB | 823855 A | 11/1959 |
| GB | 829215 A | 3/1960 |
| GB | 1520492 A | 8/1978 |
| GB | 2545456 A | 6/2017 |
| JP | S58160033 A | 9/1983 |
| JP | H05168660 A | 7/1993 |
| JP | 3094949 B2 | 10/2000 |
| JP | 2003128081 A | 5/2003 |
| JP | 2005145561 A | 6/2005 |
| JP | 2007262603 A | 10/2007 |
| JP | 2010222006 A | 10/2010 |
| JP | 2014198588 A | 10/2014 |
| JP | 2015227517 A | 12/2015 |
| JP | 2017218157 A | 12/2017 |
| KR | 20080111808 A | 12/2008 |
| NZ | 264733 A | 4/1997 |
| WO | 9210412 A1 | 6/1992 |
| WO | 9723186 A1 | 7/1997 |

(56) References Cited

FOREIGN PATENT DOCUMENTS

| WO | 02094678 | A1 | 11/2002 |
| --- | --- | --- | --- |
| WO | 02096331 | A2 | 12/2002 |
| WO | 2004103841 | A1 | 12/2004 |
| WO | 2011073808 | A2 | 6/2011 |
| WO | 2013008938 | A1 | 1/2013 |
| WO | 2013160199 | A1 | 10/2013 |
| WO | 2015088037 | A1 | 6/2015 |
| WO | 2019056351 | A1 | 3/2019 |
| WO | 2020121160 | A1 | 6/2020 |
| WO | 2021165317 | A1 | 8/2021 |
| WO | 2021172006 | A1 | 9/2021 |
| WO | 2021172075 | A1 | 9/2021 |
| WO | 2021199600 | A1 | 10/2021 |
| WO | 2021200656 | A1 | 10/2021 |
| WO | 2021200657 | A1 | 10/2021 |
| WO | 2022022884 | A1 | 2/2022 |
| WO | 2022024591 | A1 | 2/2022 |
| WO | 2022059324 | A1 | 3/2022 |
| WO | 2022129674 | A1 | 6/2022 |
| WO | 2022158102 | A1 | 7/2022 |

OTHER PUBLICATIONS

Mark J. Kirwan, "Paper and Paperboardpackaging Technology", Available on https://www.booksfree.org/wp-content/uploads/2022/02/paper_and_paperboard_packaging_technology-signed.pdf, 2005, pp. 453.

Mespack Horizontal pouch machine, Available on https://www.youtube.com/watch?v=J6FKMopcMN8.

Mespack Innovative Packaging Technologies, Available on https://www.e-morenos.com/wp-content/uploads/2017/06/NOU_cataleg_general_ENG.pdf, No Known Date, pp. 48.

Richard Coles et al. "Food Packaging Technology", available on https://kasianparto.ir/wp-content/uploads/2022/03/Food-Packaging-Technology.pdf, vol. 5, 2003, pp. 362.

Thorsten Schmidt et al. "Reliability of evaluations for the choice of system solutions at the example of automated order picking systems for bagged goods", May 30, 2014, pp. 14.

"Aegis Paper", Online retrieved from "https://www.nspackaging.com/news/mondi-aegispaper-barrier/";2021; 02 pages.

"Kraft paper", Online retrieved from "https://en.wikipedia.org/wiki/Kraft_paper"; Unknown date; 03 pages.

"Wax Paper", Online retrieved from "https://en.wikipedia.org/wiki/Waxed_paper"; Unknown date; 02 pages.

Axello Tough White White MF Kraft Paper. Specification Data [online]. BillerudKorsnas Axello, Sep. 12, 2019 [retrieved on Sep. 22, 2022]. Retrieved from the Internet :https://www.billerudkorsnas.com/packaging-materials/kraft-paper-bags/axello (Year:2019).

Axello Tough White White MF Kraft Paper. Technical Datasheet [online]. BillerudKorsnas Axello, Sep. 12, 2019 [retrieved on Jul. 27, 2022]. Retrieved from the Internet: https://www.billerudkorsnas.com/packaging-materials/kraft-paper-bags/axello (Year: 2019).

PCT Search Report and Written Opinion for PCT/US/2022/038611 dated Nov. 18, 2022, 12 pages.

* cited by examiner

SEALED ABSORBENT ARTICLE PACKAGE WITH NATURAL FIBERS

CROSS REFERENCE TO RELATED APPLICATIONS

This application claims the benefit, under 35 U.S.C. § 119(e), to U.S. Provisional Application No. 63/227,354, filed Jul. 30, 2021, which is incorporated by reference herein in its entirety.

FIELD OF THE INVENTION

The present invention pertains to disposable absorbent articles and their packaging, more particularly to packaging material for disposable absorbent articles that comprises natural fibers.

BACKGROUND OF THE INVENTION

Products which are environmentally friendly are at the forefront of many consumer's minds at this point in our history. There is an increased focus on products which are sustainably sourced. For example, there is a strong desire in the marketplace to create consumer products which comprise natural materials, bio-sourced materials, and/or recycled materials. On the disposal end, there is an increased focus on products which are bio-degradable, compostable, recyclable, reusable, and/or otherwise cause minimal landfill waste.

In the context of disposable absorbent articles, particularly disposable absorbent article packaging, there are package materials which already satisfy one or both of these criteria. For example, there are a myriad of absorbent articles which utilize carton board as their on shelf package. Carton board, as it is derived from wood pulp, may be one or both sustainably sourced and recyclable. And where the products within the package cannot form a shelf stable surface on their own, carton board is useful.

Where disposable absorbent articles are capable of being compressed and/or forming a shelf stable surface, a more flexible material is often used, i.e., plastic. Plastic is generally preferred over carton board because plastic can withstand the rigors of a packaging process much more so than carton board given the plastic's ability to flex and stretch. However, there is growing public demand for alternatives to plastic and non-plastic based materials. Flexible packaging materials which are natural based would satisfy that demand.

SUMMARY OF THE INVENTION

Packages of the present disclosure comprise one or more absorbent articles therein and comprise a package material comprising natural fibers. Each of the packages comprises a plurality of panels, including a consumer-facing panel, and wherein the package is sealed. Additionally, the packages of the present disclosure are recyclable.

In one example, a package of one or more absorbent articles, wherein the one or more absorbent articles are sealed within the package, the package comprises: a plurality of panels, including a consumer-facing panel and a top panel disposed superjacent to the consumer-facing panel, wherein each of the plurality of panels comprises an inner surface and an outer surface; a top fold line disposed between the consumer-facing panel and the top panel, wherein the top fold line is colinear, at least in part, with a cross-wise crease; and wherein the package material comprises natural fibers and has a basis weight of between 60 gsm to 120 gsm, more preferably between 65 gsm to 105 gsm, or most preferably between 70 gsm to 90 gsm, as determined via ISO 536 as modified herein.

DETAILED DESCRIPTION OF THE INVENTION

Figure 1:
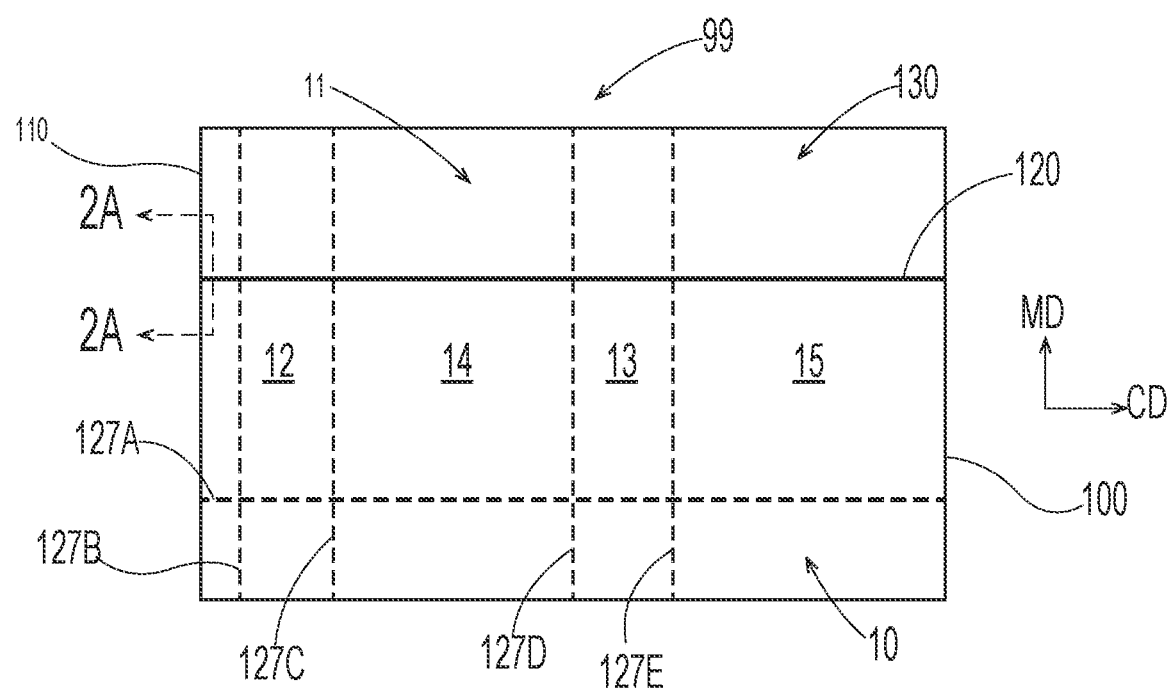
FIG. 1 is a schematic representation showing a web of package material in accordance with the present description showing an inner surface of the package material.

The term "absorbent article" as used herein refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, diaper outer covers, absorbent inserts for the diaper outer covers, menstrual pads, incontinence pads, liners, pantiliners, tampons, durable menstrual pants, and the like.

The term "crease" refers to a feature or features in a web material that create an axis of preferential bending of the web. Creases of the present disclosure may comprise embossed areas, lower caliper areas, areas of less density, areas of less stiffness, areas of material displacement or combinations thereof. It is worth noting that creases are present in the webs of the present disclosure prior to folding, while folds are only present after the folding of the web.

The term "cross-machine direction" or "CD", as used herein, refers to the path that is perpendicular to the machine direction in the plane of the web.

The term "machine direction" or "MD", as used herein, refers to the path that material, such as a web, follows through a manufacturing process.

The term "colorant", as used herein, refers to inks, dyes, pigments, or the like, used to create color in a substrate.

The term "natural fibers" as used herein, refers to fibers which comprise cellulose-based fibers, bamboo based fibers, and the like. Natural fibers also refers to nonwoody fibers, such as cotton, abaca, kenaf, sabai grass, flax, esparto grass, straw, jute hemp, bagasse, milkweed floss fibers, and pineapple leaf fibers; and woody, wood, or pulp fibers such as those obtained from deciduous and coniferous trees, including softwood fibers, such as northern and southern softwood kraft fibers; hardwood fibers, such as *eucalyptus*, maple, birch, and aspen. Pulp fibers can be prepared in high-yield or low-yield forms and can be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it can be desirable that the natural fibers be relatively undamaged and largely unrefined or only lightly refined. The fibers can have a Canadian Standard Freeness of at least 200, more specifically at least 300, more specifically still at least 400, and most specifically at least 500.

The term "cellulose-based fibers," as used herein, may include cellulose fibers such as wood fiber, cotton, regenerated cellulose fiber such viscose, lyocell, rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

The terms "non-recyclable material" or "contaminant" as used herein, refers to materials which are believed to be unsuitable for processing in the natural fiber recycling process. However, in alternative recycling streams, the materials provided with one or both of these designations may be recyclable.

The package material of the present disclosure can provide a premium look to finished packages where the package material comprises natural fibers. The package material of the present disclosure can facilitate processing of the package material by allowing for tighter tolerances regarding fold line positioning as well as potentially allow for the reduction of adhesive usage.

The package material of the present disclosure comprises at least one crease to facilitate folding of the package material along the crease. For the sake of clarity, a crease is a feature provided on the package material which facilitates folding of the package material once products are placed therein or prior to their placement therein. A fold line that is associated with the crease is generally colinear with the crease.

Creases can be created via any suitable method. In one example, the creases may be created via embossing of the package material. In such processes, the package material may be passed through a pair of rollers, wherein at least one of the rollers compresses a portion of the package material. This area of compressed package material can create a hinge or preferential bending axis for the subsequent fold line. Another suitable process for creating creases in accordance with the present disclosure is displacement. For example, the package material may comprise an area of material which is displaced in a thickness direction. The displaced material may comprise the crease. In such executions, in contrast to embossing of the creases, the creases may comprise an area of lower density, e.g., bottom surface of the crease. These creases can provide a preferential bending axis for one or more fold lines. Another suitable method includes skiving where the creases comprise reduced thickness based on the removal of material in the crease. Again, any suitable method for creating one or more creases in the packages of the present disclosure may be utilized, e.g., lasers or other mechanical treatments, chemical treatments, and/or combinations thereof.

The inventors have surprisingly found that placement of creases in particular areas of the package material can provide a more finished looking package. For example, edges of the package are much more defined and the panels of the package appear much more purposeful rather than haphazard. Additionally, the inventors have found that there is a reduced amount of gusset offset when sealing the packages. This can result in less quality outages which allows for more production time. Also, the inventors have also surprisingly found that with strategic placement of creases, packages comprising the package material of the present disclosure can be more easily stacked.

The package material of the present disclosure may be configured to comprise a generally cuboid shape, i.e., having a plurality of panels. Packages in such configurations may comprise the consumer-facing panel. As noted previously, the consumer-facing panel is the face of the package that faces the consumer. In general, the consumer-facing panel comprises branding and/or package information, each of which is discussed in additional detail herein. Each of the plurality of panels comprises an inner surface and an outer surface.

In addition to the consumer-facing panel, the packages of the present disclosure may further comprise a back panel opposing the consumer-facing panel, a left panel disposed between the consumer-facing panel and the back panel, a right panel opposing the left panel, a bottom panel disposed between the consumer-facing panel and the back panel, and an opposing top panel. The top panel may comprise an opening tail as well as side gussets. The opening tail and side gussets are discussed in additional detail hereafter. Additional package configurations are also disclosed hereafter.

Additional features of the packages of the present disclosure include edges, particularly where these packages comprise a generally cuboid shape. For example, a first edge may be positioned between the consumer-facing panel and the right panel; a second edge may be positioned between the right panel and the back panel, a third edge may be positioned between the back panel and the left panel, and a fourth edge may be positioned between the left panel and the consumer-facing panel.

The package material may be unitary. For example, multiple folds may be utilized to form the edges between the plurality of panels of the package. To further elucidate the example where the package is a cuboid shape, at least one fold may be disposed between each of the panels. For example, a top fold line may be positioned adjacent a top edge of the one or more absorbent articles within the package. The top fold line may comprise a first portion disposed between the consumer-facing panel and the top panel, a second portion between the right panel and the top panel, a third portion between the back panel and the top panel, and a fourth portion between the left panel and the top panel. It is worth noting that in some forms, the package material may comprise discrete portions. Package material configurations will be discussed in additional detail hereafter.

In order to create more defined panels of the packages of the present disclosure, a cross-wise crease may be positioned between a pair or several pairs of panels of the package. As an example, the cross-wise crease may comprise a first section disposed between the consumer-facing panel and the top panel. The first section may comprise a first part and a second part. The first part may extend from the fourth edge toward a centerline of the consumer-facing panel. The second part may extend from the first edge toward a centerline of the consumer-facing panel. The first section of the cross-wise crease and the first portion of the top fold line can be colinear.

The relationship of the first portion of the top fold line and the first section of the cross-wise crease can vary. The first portion of the top fold line, in order to create a sustainable shape, can preferably have a length which is the length of the overall package. However, the first section is not necessarily required to extend the full length of the package. Instead, as the cross-wise crease is provided to encourage folding about the cross-wise crease, the first part and second part of the cross-wise can have a cumulative length which is less than the length of the first portion of the top fold line. For example, the first part and second part of the first section of the cross-wise crease can have a cumulative length which is at least 10 percent of the length of the first portion of the top fold line, more preferably at least 30 percent of the length of the first portion of the top fold line, or most preferably at least 50 of the length of the first portion of the top fold line, specifically reciting all values within these ranges and any ranges created thereby. In one specific example, the first portion of the top fold line and the first section of the cross-wise crease may be coextensive. In such examples, the first portion of the top fold line and the first section can extend the full length of the package.

Regarding the transition between the right panel and the top panel, the top fold line may comprise a second portion, and the cross-wise crease may comprise a second section. The second portion of the top fold line and the second section of the cross-wise crease may be colinear.

The second section of the cross-wise crease may comprise a first part and a second part. The first part may extend from the first edge toward a vertical centerline of the right panel, and the second part may extend from the second edge toward the vertical centerline of the right panel. The second portion may have a length which is equal to the overall depth of the package. In contrast, the first part and the second part of the second section of the cross-wise crease may comprise a cumulative length which is at least 10 percent of the length of the second portion of the top fold line, more preferably at least 30 percent of the length of the second portion top fold line, or most preferably at least 50 of the length of the second portion of the top fold line, specifically reciting all values within these ranges and any ranges created thereby. In one specific example, the second portion of the top fold line and the second section of the cross-wise crease may be coextensive. In such examples, the second portion of the top fold line and the second section of the cross-wise crease may extend the full depth of the package.

For the sake of brevity, the relationship between the left panel and the top panel may be as described in the foregoing regarding the relationship of the right panel and the top panel. However, in this relationship, the top fold line may comprise a fourth portion and the cross-wise crease may comprise a fourth section. The fourth section may comprise a first part and a second part, the first part may extend from the third edge toward a vertical centerline of the left panel, and the second part may extend from the fourth edge toward the vertical centerline of the left panel.

Regarding the back panel and the top panel, the top fold line may comprise a third portion and a cross-wise crease may comprise a third section. The third section may comprise a first part and a second part. The first part may extend from the second edge toward a vertical centerline of the back panel, and the second part may extend from the third edge toward the vertical centerline of the back panel. The third portion may comprise a length which is the same as the first portion of the top fold line. The cumulative length of the first part and the second part of the third section of the cross-wise crease may be at least 10 percent of the length of the third portion of the top fold line, more preferably at least 30 percent of the length of the third portion top fold line, or most preferably at least 50 of the length of the third portion of the top fold line, specifically reciting all values within these ranges and any ranges created thereby. In one specific example, the third portion of the top fold line and the third section of the cross-wise crease may be coextensive. In such examples, the third portion of the top fold line and the third section of the cross-wise crease may extend the full length of the package.

The top fold line and the cross-wise crease are colinear to the extent the package comprises cross-wise creases. For example, some packages may comprise only the first section of the cross-wise crease to create a more defined looking consumer-facing panel and may not provide the second, third, or fourth section of the cross-wise crease. Or, some packages may provide the first section, second sections, and fourth sections of the cross-wise crease. Any suitable independent or combination of cross-wise crease sections may be utilized.

The cross-wise crease may be disposed adjacent a top edge of the one or more absorbent articles within the package. For example, the one or more absorbent articles within the package comprise a top edge and an opposing bottom edge, wherein the bottom edge is disposed more proximal to the bottom panel than the top edge. A first plane may comprise the cross-wise crease, and a second plane may comprise the top edge of the absorbent articles, wherein the first plane and the second plane are generally horizontal and parallel to one another. A distance between the first plane and the second plane can be about 5 mm or less, more preferably about 3 mm or less, or most preferably about 2 mm or less, specifically reciting all values within these ranges and any ranges created thereby. It is worth noting that the foregoing distances between the first plane and the second plane are the absolute values of the distance. So, in some instances the first plane may be more proximal to the bottom panel than the second plane or vice versa.

In order to create a more shelf stable display where packages of the present disclosure are stacked one on top of the other, an additional crease may be utilized. For example, where the packages of the present disclosure comprise opening tails (described hereafter), an additional crease—an opening crease—may be utilized. The opening crease can be created to help the opening tail lay flatter. The flatter the opening tail lays, the more stable a stacked package thereon will be.

To minimize the likelihood of contamination of the one or more absorbent articles within the package, the opening tail may comprise a seal, e.g., via adhesive or barrier film. The opening tail comprises package material which is sealed together to form an access seal. Because the opening tail comprises multiple layers of package material joined together, the opening tail can be much stiffer than a single layer of the packaging material. These stiffer tails can resist folding down and tend to spring back upright thereby "kicking" off packages which are on top of the opening tail. To alleviate the "kick" of the opening tail, the opening tail and/or the top panel may comprise a crease which facilitates the folding thereof, i.e., the opening crease.

In addition to the opening tail, the top panel may further comprise a front face, an opposing back face, a right face, and an opposing left face. An opening crease may be provided on a front face which facilitates folding of the opening tail toward the back face. Forms are also contemplated where the opening crease is provided on the back face, the left face, the right face, each independently or any combinations thereof. And much like the cross-wise crease, the opening crease may have a cumulative length which is shorter than the fold associated with the opening crease, i.e. an opening fold. For example, cumulative length of the opening crease on any face of the opening tail may be at least 10 percent of the length of the opening fold, more preferably at least 30 percent of opening fold, or most preferably at least 50 of the length of the opening fold, specifically reciting all values within these ranges and any ranges created thereby. In one specific example, the opening crease and the opening fold line may be coextensive. The opening fold line may be configured similar to the top fold line, e.g., comprising a first portion, second portion, etc., and the opening crease may be configured similar to the cross-wise crease, e.g., comprising a first section, second section, etc., wherein each section comprises a first part and a second part.

Additional creases may be provided to the packages of the present disclosure. For example, the left face and/or right face may comprise gusset creases. The gussets creases can ensure that interior gusset folds are approximately equal from the front face to the back face of the top panel. This reduces the variability of the gusset folds and helps to ensure that the interior gusset folds look symmetrical and provide a more finished look to the package.

It is worth noting that depending on the type of package created, additional creases to the ones described herein may be desired. As an example, where a manufacturer of absorbent articles obtains bags comprising a block bottom configuration (discussed in additional detail herein), each of the bags may comprise vertical creases which when folded form the first, second, third, and fourth edges. Additionally, these vertical creases, when folded, may form exterior gusset folds on the left and right faces of the top panel. And block bottom configuration bags may comprise a bottom crease as well which helps to create a flat bottom panel.

Additionally, bags comprising a cross bottom configuration (discussed in additional detail herein), may be utilized. Cross bottom configuration bags may comprise vertical creases which fall generally along a centerline of a panel, e.g., right panel and/or left panel. In such configurations, the manufacturer may request from the package material manufacturer, additional vertical creases to be added similar to the block bottom configuration packages. These additional vertical creases may be provided to form the first, second, third and/or fourth edges once the package material is folded. Additionally, cross bottom configuration bags may comprise a bottom crease which creates a flat bottom panel.

In yet another execution, pinch bottom configuration (discussed in additional detail herein) may be utilized. Such packages may comprise a crease on the bottom panel which generally bisects the depth of the bottom panel. In such configurations, manufacturers may seek the provision of vertical creases to form the first, second, third and/or fourth edges. Additionally, or independently thereof, manufacturers may also seek the provision of a bottom crease which can create a more defined/flat bottom panel. The bottom crease may be configured similar to the cross-wise crease, e.g., comprising a first section, second section, etc. And a bottom fold may be positioned colinearly with the bottom crease. The bottom fold may be configured similar to the top fold line, e.g., comprising a first portion, second portion, etc.

In yet another execution, stand-up pouch configuration, seals may be formed along the bottom panel and the side panels. In such configurations, the manufacturer of absorbent articles or packager thereof, may request for these bags to include vertical creases corresponding to the edges described herein.

Still other executions are possible. For example, rather than receiving preformed bags, an absorbent article manufacturer may choose to form the packages from a web of package material, e.g., a roll of package material. In such instances, the manufacturer may choose to either block bottom, cross bottom, pinch bottom or stand-up pouch configurations for their bags and add one or more of the creases described herein to provide a more defined look amongst the panels of the package and to facilitate stacking of the packages.

Alternatively, the absorbent article manufacturer can utilize a flow wrap method for packaging of the one or more absorbent articles. In such configurations, the package material is in roll form. The one or more absorbent articles are placed on a web of the package material, and the package is then formed about the one or more absorbent articles. In order to facilitate the folding of the package and the creation of the panels as described herein, the absorbent article manufacturer may provide one or more of the creases described herein to the web of package material prior to the formation of the package about the one or more absorbent articles.

Additionally, while the prior discussion pertains to packages which are generally cuboid in shape, other package shapes are contemplated. For example, package shapes comprising less than six panels are contemplated. Building on this example, packages having a circular or semi-circular shape when viewed from a bottom panel are contemplated. Additionally, packages having a triangular shape when viewed from the bottom panel are contemplated. Regardless of the number of panels comprised by the packages of the present disclosure, the package comprises a consumer-facing panel. And as disclosed herein, a cross-wise crease may be provided between the consumer-facing panel and the top panel.

Data provided in Table 1 demonstrates the effectiveness of the addition of creases to package materials of the present disclosure. All measurement in Table 1 were taken via the Bag Compression method described herein.

TABLE 1

|  | Initial Height at 0.2N mm | Force at Compression Height N | Normalized Force at Compression Height N/cm | Energy of Compression N*mm | Final Height at 0.2N mm | Energy of Compression N*mm |
|---|---|---|---|---|---|---|
|  |  |  | w/crease |  |  |  |
| Ave | 94.7 | 3.6 | 0.39 | 10.3 | 83.7 | 0.20 |
| St Dev | 2.7 | 0.9 | 0.10 | 2.4 | 0.4 | 0.13 |
|  |  |  | w/o crease |  |  |  |
| Ave | 102.5 | 5.1 | 0.55 | 17.3 | 84.6 | 0.61 |
| St Dev | 4.2 | 2.1 | 0.23 | 10.6 | 1.2 | 0.54 |

Energy of Compression demonstrates that the package material of the present disclosure, i.e., comprising one of more of the creases described herein, is easier to compress than the bag without creases. The bag with creases has an Energy of Recovery that is less than the bag without creases. This means that the bag without creases has a greater desire (and ability) to press back "up" vs the bag with creases (bag without creases is pushing back at a greater force vs the creased bag).

TABLE 2

| Sample | Sample Size (mm) | Peak Load (N) | Energy to Peak (N*mm) | Slope (N/mm) |
|---|---|---|---|---|
| Non-creased bag material | 80 × 40 | 1.992 ± 0.063 | 1.566 ± 0.104 | 2.839 ± 0.077 |
| Non-creased bag material | 70 × 30 | 2.065 ± 0.106 | 1.520 ± 0.182 | 2.715 ± 0.121 |
| Crosswise crease, front of bag | 80 × 40 | 1.495 ± 0.078 | 1.271 ± 0.100 | 2.017 ± 0.198 |
| Crosswise crease, back of bag | 70 × 30 | 1.345 ± 0.124 | 1.075 ± 0.153 | 1.950 ± 0.147 |
| Opening Crease, back of bag | 70 × 30 | 1.644 ± 0.092 | 1.309 ± 0.210 | 2.136 ± 0.084 |

It is worth noting that the creases of the present disclosure have a preferential bending direction. Specifically, folding in the direction of the crease can provide lower forces for folding/recovery. Folding against the direction of the crease can similarly provide lower forces for folding/recovery; however, the reduction is not as great as the former. Data demonstrating this is shown in Table 3 in the that samples with the creases were folded against the crease.

TABLE 3

| Sample | Sample Size (mm) | Peak Load (N) | Energy to Peak (N*mm) | Slope (N/mm) |
|---|---|---|---|---|
| Non-creased bag material | 80 × 40 | 1.992 ± 0.063 | 1.566 ± 0.104 | 2.839 ± 0.077 |
| Non-creased bag material | 70 × 30 | 2.065 ± 0.106 | 1.520 ± 0.182 | 2.715 ± 0.121 |
| Crosswise crease, front of bag | 80 × 40 | 1.662 ± 0.195 | 1.365 ± 0.190 | 2.211 ± 0.268 |
| Crosswise crease, back of bag | 70 × 30 | 1.461 ± 0.166 | 1.278 ± 0.173 | 1.999 ± 0.244 |

TABLE 3-continued

| Sample | Sample Size (mm) | Peak Load (N) | Energy to Peak (N*mm) | Slope (N/mm) |
|---|---|---|---|---|
| Opening Crease, back of bag | 70 × 30 | 1.606 ± 0.139 | 1.356 ± 0.199 | 2.155 ± 0.241 |

The data in both Table 2 and 3 was obtained using the Bending Method disclosed herein.

Further building on folding in the direction of the crease or against the direction of the crease, the term "bias" is used herein. A crease that is biased from the inner surface toward the outer surface of the package material means the package material within the crease is recessed from the inner surface. In contrast, a crease that is biased from the outer surface toward the inner surface of the package material means the package material within the crease is recessed from the outer surface. This is further explained with regard to FIGS. 2A, 2B and 5B.

As shown in Tables 2 and 3, the cross-wise crease may exhibit a Peak Load of about 1.8 N or less, or more preferably about 1.7 N or less, specifically reciting all values within these ranges and any ranges created thereby. For example, the cross-wise crease may exhibit a Peak Load of from about 0.7 N to about 1.8 N or more preferably from about 0.8 N to about 1.7 N, specifically reciting all values within these ranges and any ranges created thereby. It is worth nothing that the opening crease may exhibit similar Peak Load values to those of the cross-wise crease.

Additionally, the cross-wise crease may exhibit a slope of about 2.5 N/mm or less, more preferably about 2.4 N/mm or less or most preferably about 2.3 N/mm or less, specifically reciting all values within these ranges and any ranges created thereby. For example, the cross-wise crease may exhibit a slope of from about 1.5 N/mm to about 2.5 N/mm, more preferably from about 1.6 N/mm to about 2.4 N/mm or most preferably from about 1.7 N/mm to about 2.3 N/mm, specifically reciting all values within these ranges and any ranges created thereby. Much like the foregoing, the opening crease may exhibit a similar slope to that of the cross-wise crease.

As noted previously, the creases may be provided to the package material as noted herein via any suitable process. Additionally, the creases of the present disclosure may have any suitable width. For example, the creases may comprise a width of 7 mm or less, preferably of 5 mm or less, more preferably 3 mm or less, or most preferably 2 mm or less, specifically reciting all values within these ranges and any ranges created thereby. In such configurations, the creases of the present disclosure may comprise a width of from about 0.1 mm to about 7 mm, more preferably from about 0.1 mm to about 5 mm or most preferably from about 0.1 mm to about 4 mm, specifically reciting all values within these ranges and any ranges created thereby. In one specific example, the creases of the present disclosure may comprise width from about 0.1 mm to about 3 mm, more preferably from about 1 mm to about 2 mm, or most preferably from about 0.1 mm to about 1 mm, specifically reciting all values within these ranges and any ranges created thereby.

It is worth noting that the creases of the present disclosure are not required to have the same width. For example, the cross-wise crease may comprise a first width while the opening crease may comprise a second width, wherein the first width and the second width albeit within the above ranges are different. Similarly, where a crease of the present disclosure comprises a plurality of sections as described herein, each section may comprise variable width. Moreover, a particular section of a crease may have a variable width. For example, the first part of the first section of the cross wise crease may comprise a first crease width adjacent the fourth edge and a second crease width as the first part extends toward the vertical centerline of the consumer-facing panel, wherein the first crease width is different than the second crease width. Any section of a crease may be configured in this manner.

The creases of the present disclosure may comprise a depth of greater than about 0.01 mm, more preferably greater than about 0.02 mm, or most preferably greater than about 0.03 mm, specifically reciting all values within these ranges and any ranges created thereby. For example, the creases of the present disclosure may comprise a depth of from about 0.01 mm to about 0.9 mm, more preferably from about 0.02 mm to about 0.7, or most preferably from about 0.03 mm to about 0.5 mm, specifically reciting all values within these ranges and any ranges created thereby. The width and/or depth of the creases of the present disclosure may be measured via the Crease Dimensions Using CLSM method disclosed herein.

Package Material

In order to withstand the rigors of a manufacturing process where a plurality of absorbent articles is disposed within the package, withstand the rigors of being shipped, provide protection from environmental insults during shipping and while on the store shelf, and provide for product protection while in the consumers home, the package material may have some level of strength, stretch, and resilience. As an example, package material of the present disclosure may exhibit an MD tensile strength of at least 4.7 kN/m, more preferably at least 7 kN/m, or most preferably at least 8 kN/m, specifically reciting all values within these ranges and any ranges created thereby. The MD tensile strength may be between 4.7 kN/m to 8.5 kN/m, or more preferably between 5.2 kN/m and 8.2 kN/m, or most preferably between 5.5 kN/m and 8.0 kN/m, specifically reciting all values within these ranges and any ranges created thereby. The MD tensile strength is measured using ISO 1924-3 as modified herein.

As another example, the package material of the present disclosure can exhibit a CD tensile strength of at least 2.7 kN/m, more preferably at least 4 kN/m, or most preferably at least 5.5 kN/m, specifically reciting all values within these ranges and any ranges created thereby. The CD tensile strength may be between 2.7 to 6.5 kN/m, more preferably between 2.7 to 6.2 kN/m, or most preferably between 2.7 to 6 kN/m, specifically reciting all values within these ranges and any ranges created thereby. The CD tensile strength is measured using ISO 1924-3 as modified herein.

As another example, the package material of the present disclosure can exhibit a burst strength of at least 185 kPa, more preferably at least 250 kPa, or most preferably at least 550 kPa, specifically reciting all values within these ranges and any ranges created thereby. The burst strength of the package material of the present disclosure can be between 185 to 600 kPa, more preferably between 220 to 550 kPa, or most preferably between 250 to 500 kPa, specifically reciting all values within these ranges and any ranges created thereby. The burst strength is measured using ISO 2758 as modified herein.

As another example, the package material of the present disclosure may exhibit an MD stretch at break, more preferably at least 3 percent, or most preferably at least 6 percent, specifically reciting all values within these ranges and any ranges created thereby. The package material of the present disclosure can exhibit an MD stretch at break of between 3 to 6.5 percent, more preferably between 3.2 to 6.2 percent, or most preferably between 3.5 to 6 percent, specifically reciting all values within these ranges and any ranges created thereby. The MD stretch at break is measured using ISO 1924-3 as modified herein.

As another example, the package material of the present disclosure can exhibit a CD stretch at break of at least 4 percent, more preferably at least 6 percent, or most preferably at least 9 percent, specifically reciting all values within these ranges and any ranges created thereby. The package material of the present disclosure can exhibit a CD stretch at break of from 4 to 10 percent, more preferably from 4.5 to 9.5 percent, or most preferably from 5 to 9 percent, specifically reciting all values within these ranges and any ranges created thereby. The CD stretch at break is measured using ISO 1924-3 as modified herein.

As yet another example, the basis weight of the package material can affect the "feel" of the package to the consumer in addition to affecting the strength and resilience of the package material. Too low of a basis weight and the package can feel too flimsy. Too high and the package can feel too inflexible. The package material of the present disclosure can have a basis weight of between 50 to 120 gsm, more preferably between 60 to 105 gsm, or most preferably between 70 to 90 gsm, specifically reciting all values within these ranges and any ranges created thereby. The basis weight can be determined via ISO 536 as modified herein.

It is worth noting that the lower basis weight of 50 gsm may require some precautions during processing. For high speed packaging processes, a basis weight of 50 gsm may not provide the desired level of reliability. It is believed that high speed packaging processes may induce strain into the packaging material that slower packaging processes may not. So from a high speed manufacturing standpoint, 60 gsm may be the lowest desirable package material basis weight. Where hand packing or lower speed packaging processes are utilized, 50 gsm may be sufficient as the lowest package material basis weight. Or, special processing and/or tooling which is tightly controlled to ensure that minimal strain is applied to the 50 gsm or lower package material may be sufficient to allow 50 gsm package material to be utilized.

Regarding caliper, the package material of the present disclosure can exhibit caliper of at least 50 μm, more preferably at least 70 μm, or most preferably at least 90 μm, specifically reciting all values within these ranges and any ranges created thereby. The package material of the present disclosure can exhibit caliper of between 50 to 110 μm, more preferably from 55 to 105 μm, or most preferably from 60 to 100 μm, specifically reciting all values within these ranges and any ranges created thereby. The caliper is measured using ISO 534 as modified herein.

It is worth noting that the package material of the present disclosure is different than cartonboard, cardboard, and brown paper bags. For example, cartonboard is not as flexible as the package materials of the present disclosure. Cartonboard is designed and is inherently stiffer than the package materials of the present disclosure and can be more difficult to process on converting lines due to their stiffness. Additionally, cartonboard has a higher basis weight than does the package materials of the present disclosure.

Similarly, cardboard is also different than the package materials of the present disclosure. Cardboard has a much higher basis weight than those of the package materials of the present disclosure. Additionally, cardboard is much less flexible than the package materials of the present disclosure. Cardboard materials are commonly fluted and comprise three plies of a paper material and as such, is structurally different than the package materials of the present disclosure. Additionally, the package material of the present disclosure has a much lower basis weight than does cardboard.

Some advantages that the packaging material of the present disclosure have over cartonboard and cardboard include the flexibility as discussed herein. However, another advantage is that the package materials of the present disclosure take up less space than their more-bulky cartonboard and cardboard counterparts. Another advantage of the package materials of the present disclosure is that they allow the absorbent articles therein to be compressed within the package. This allows for more products to fit within a smaller volume package which also enable efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Regarding brown paper bags which were prevalent in grocery stores for carrying groceries, the packages of the present disclosure are also different. As discussed in additional detail herein, the package material of the present disclosure is sealed such that the absorbent articles are enclosed and protected from the external environment by the package material. More specifically, the package of absorbent articles in accordance with the present disclosure does not have an opening into which items can be placed. Instead, the package of absorbent articles in accordance with the present disclosure is sealed to reduce the likelihood of contamination of the absorbent articles during shipping, stocking, and sitting on store shelves.

Despite having reduced flexibility compared to plastic packaging and lower basis weight than cardboard and cartonboard, the inventors have surprisingly found the packaging material of the present disclosure can withstand the rigors of a manufacturing process where one or more absorbent articles is placed within the package as well as the rigors of being shipped, provide protection from environmental insults during shipping, and while on the store shelf, and provide for product protection while in the consumers home.

It is also worth noting that the package material of the present disclosure, in addition to lacking the high stretch properties of conventional plastic packaging film, may not provide the barrier properties of a conventional plastic packaging film. For example, the package material of the present disclosure may not comprise a functional, barrier layer such as a layer of foil, plastic, or the like. However, forms are contemplated where the packaging material of the present disclosure comprises an outer material comprising natural fibers and a barrier layer of material, e.g., polyethylene based plastic.

In addition, examples are contemplated where the absorbent article backsheet is in direct contact with the inner surface of the package material. Packages of the present disclosure comprising diapers may be configured in this manner Feminine hygiene pads, including menstrual pads, liners, adult incontinence pads, and the like, may be individually wrapped in order to protect panty fastening adhesive on their respective backsheets. In packages with these articles, the individually wrapped article may be in direct contact with the inner surface of the package material. Forms are contemplated where the wrapper which wraps the individual articles may comprise natural fibers as described herein. Additionally, such wrappers may be recyclable as described herein.

Recyclability

There is currently no universal standard for determining whether a paper material is recyclable. In general, the higher the content of natural material, e.g., natural fibers, and the lower the content of non-recyclable material, the higher the likelihood of being recyclable. Some specific examples of standards which may be useful in determining whether package material is recyclable include the PTS method and Western Michigan method, and each is described below in additional detail. These methods pertain to the recyclability of materials which comprise wood fibers and/or pulp fibers.

Package materials of the present disclosure may comprise natural fibers which form a paper. The package material may comprise at least 50 percent by weight natural fibers, more preferably at least 70 percent by weight natural fibers, or most preferably at least 90 percent by weight natural fibers, specifically reciting all values within these ranges and any ranges created thereby. As yet another example, the package material may comprise 99.9 percent by weight natural fibers. The package materials of the present disclosure may comprise between 50 percent by weight to 100 percent by weight natural fibers, more preferably between 70 percent by weight to 99.9 percent by weight, or most preferably between 90 percent by weight to 99.9 percent by weight natural fibers. It is worth noting that where the weight percentage of natural fibers is less than 100 percent, there is room for coatings, colorants, and/or adhesives, if desired.

In order to increase the likelihood that the package material is recyclable, the total weight percentage of non-recyclable material, e.g., adhesives, coatings and/or colorants, in the package material of the present disclosure may be carefully selected. For example, the package material of the present disclosure may comprise 50 percent by weight or less, more preferably 30 percent by weight or less, or most preferably about 15 percent by weight or less of non-recyclable material, specifically including all values within these ranges and any ranges created thereby. As another example, the package materials of the present disclosure may comprise from between about 0.1 percent to about 50 percent by weight, more preferably from about 0.1 percent to about 30 percent by weight, or most preferably from about 0.1 percent to about 15 percent by weight of non-recyclable material, specifically including all values within these ranges and any ranges created thereby. In one specific example, the weight percentage of non-recyclable materials can be 5 percent by weight or less, or between 0.1 percent to 5 percent by weight, specifically reciting all values within these ranges and any ranges created thereby.

The effectiveness of the recycling process on the package material of the present disclosure may be determined via recyclable percentage. Package material of the present disclosure can exhibit recyclable percentages of 70 percent or greater, more preferably 80 percent or greater, or most preferably 90 percent or greater, specifically reciting all values within these ranges and any ranges created thereby. The packaging material of the present disclosure can have a recyclable percentage of between 70 percent to about 99.9 percent, more preferably from about 80 percent to about 99.9 percent, or most preferably from about 90 percent to about 99.9 percent, specifically reciting all values within these ranges and any ranges created thereby. In one specific example, the package material of the present disclosure may exhibit a recyclable percentage of from about 95 percent to about 99.9 percent, more preferably from about 97 percent to about 99.9 percent, or most preferably from about 98 percent to about 99.9 percent, specifically including all values within these ranges and any ranges created thereby. The recyclable percentage of the package material of the present disclosure can be determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage can be determined via the PTS-RH:021/97 (Draft October 2019) under category II, test method. However, unlike the recyclable percentage, in order to increase the likelihood of recyclability, the total reject percentage can be decreased. For example, the total reject percentage of the package material of the present disclosure can be about 30 percent or less, more preferably about 20 percent or less, or most preferably about 10 percent or less, specifically including all values within these ranges and any ranges created thereby. For example, the total rejection percentage of the package material of the present disclosure can be from 0.1 percent to 30 percent, more preferably from 0.1 percent to 20 percent, or most preferably from 0.1 percent to 10 percent, specifically reciting all values within these ranges and any ranges created thereby. In one specific example, the total reject percentage can be less than 5 percent, or between 0.1 percent to 5 percent, more preferably 0.1 to 3 percent, or most preferably 0.1 to 2 percent, specifically including all values within these ranges and any ranges created thereby.

For the sake of clarity, the percent non-recyclable material does not necessarily have a 1:1 correlation to the total reject percentage. For example, the use of dissolvable adhesives is disclosed herein. As these adhesives are designed to dissolve during the recycling process, it is theorized that these adhesives would not have an impact on the total reject percentage; however, they would contribute to the non-recyclable material weight percent.

It is worth noting that the test method PTS-RH:021/97 (Draft October 2019), under category II, test method, comprises a handsheet inspection component. Trained screeners inspect one or more handsheets of recycled package material for visual imperfections and tackiness. If the number of visual imperfections is too great or if too tacky, then the package material is rejected. If the number of visual imperfections is acceptable and the handsheet is not too tacky, in accordance with the PTS-RH:021/97 (Draft October 2019), under category II method, then the package material is approved for additional processing. The package material of the present disclosure can yield an acceptable level of visual imperfections and tackiness during this step of the PTS method such that additional processing is approved.

The package material of the present disclosure can yield the recyclable percentages mentioned heretofore as well as pass the handsheet screening method. So the package material of the present disclosure can achieve an overall score or final outcome of "pass" when subjected to the PTS-RH:021/97 (Draft October 2019), under category II, recycling test method.

It is also worth noting that there is additional method for determining the recyclable percentage of the package material of the present disclosure. The test method performed by the University of Western Michigan called the Repulpability Test can provide a percent yield of recyclable material. The package material of the present disclosure can achieve a percentage yield, in accordance with the Repulpability Test, which is greater than about 70 percent, more preferably greater than about 80 percent, or most preferably greater than about 90 percent, specifically reciting all values within these ranges and any ranges created thereby. The packaging material of the present disclosure can have a percent yield of between 70 percent to about 99.9 percent, more preferably from about 80 percent to about 99.9 percent, or most preferably from about 90 percent to about 99.9 percent, specifically reciting all values within these ranges and any ranges created thereby. In one specific example, the package material of the present disclosure can exhibit a percentage yield of recyclable material which is between 80 percent and 99.9 percent, specifically including all values within this range and any ranges created thereby. In such example, the package material may comprise a base color of brown. In another specific example, the package material of the present disclosure can exhibit a percentage yield of recyclable material which is between 85 percent and 99.9 percent, specifically including all values within this range and any ranges created thereby. In such example, the package material may comprise a base color of white. Base colors of package materials are discussed in additional detail herein.

It is contemplated that the package material of the present disclosure, while being recyclable, may itself comprise recycled material. Such determination can be made from a visual inspection of the package material. For example, manufacturers typically advertise the use of recycled materials in an effort to demonstrate their eco-friendly packaging approach. To further expand on this example, some manufacturers may utilize a logo, e.g., a leaf, along with wording to indicate the use of recycled material in the package material. Often times, manufacturers may specify the percentage of recycled material utilized as well, e.g., over 50 percent, over 70 percent, etc.

Visual inspection can be as simple as utilizing the human eye to inspect packages for logos of the use of recycled material. Additionally or alternatively, visual inspection may include microscopy methods such as optical microscopy, scanning electron microscopy or other suitable methods known in the art. For example, package material comprising recycled paper fibers could look different under a microscope due to the presence of a much wider range of natural fiber types than if the package material comprised 100% non-recycled paper. As another example, under a microscope, potentially scanning electron microscope, recycled fibers, due to their processing may appear more fibrillated than their virgin fiber counterparts.

Seals/Adhesives

Additionally, the packages of the present disclosure comprise a plurality of seals. The seals of the packages of the present disclosure comprise seams which have been attached/joined together. Seams are areas of the package where at least two portions of the package material have the ability to overlap one another. Seals are created when the at least two portions of the package material in the seam are joined to one another. For example, the bottom panel may comprise seams where ends of the package material overlap. An adhesive may be provided on an interior surface of a first portion of the bottom panel and on an exterior surface of a second portion of the bottom panel as well as on an exterior surface of a base portion of the bottom panel to create one or more seals. Alternatively, particularly where the package material of the present disclosure comprises a plastic barrier layer, the plastic layer may be utilized in place of an adhesive. As an example, a polyethylene plastic layer can be heat sealed to itself.

The top panel may comprise seals where ends of the package material are joined together similar to the seals of the bottom panel. While the seals may be provided on any panel of the package, it is recommended that the consumer-facing panel not include seams or seals. Seams and seals can be visibly non-appealing for consumers, particularly where the seams or seals extend through a portion of the consumer-facing panel which comprises product information.

It is worth noting that seams may comprise overlap areas of package material as described heretofore. Namely, an inner surface of a first portion of the package material and an outer surface of a second portion of the package material can be joined together to create an overlap seal. However, butt seals may also be created. Butt seals can be created where the inner surface of a first portion of the package material and the inner surface of a second portion of the package material are joined together. Butt seals and overlap seals are discussed in additional detail hereafter.

The seals are important to reduce the likelihood of contamination of the absorbent articles within the package by the external environment. The use of seals, as described herein, can provide adequate sealing of the package material such that absorbent articles within the package are not exposed to the exterior environment or at least have reduced likelihood of exposure to the outside environment. Simply folding or rolling of the package material does not form a seal and is not sufficient unless seals as described herein are created.

Regarding the types of seals, the plurality of seals of the packages of the present disclosure may comprise an access seal, a hoop seal, and a bottom seal. The access seal may be provided as a seal which is opened by the consumer to access the one or more absorbent articles within the package. The hoop seal can be the initial seal created in the package making process. The bottom seal may can be located on the bottom panel. Flow wrap packages may be configured to comprise these seals as well. Or, the flow wrap packages may comprise a pair of opposing end seals and a hoop seal between the end seals. In this configuration, an access seal may similarly be provided. A variety of package configurations and their respective seals are discussed in additional detail regarding FIGS. 6-10B.

Where it is desired that the package material of the present disclosure be recyclable, the type as well as amount of adhesive utilized for the seals can be of import. As an example, adhesives which can dissolve in water during the re-pulping stage of the disintegration step of the recycling process may be particularly suitable for the package seals of the present disclosure. Such adhesives include starch based adhesives, polyvinyl alcohol based adhesives, and polyethylene oxide based adhesives. One suitable example of a starch based adhesive is available from LD Davis located in Monroe, North Carolina, under the trade name AP0420CR. One suitable example, of a polyvinyl alcohol based adhesive is available from Sekisui Chemical Company, located in Osaka, Japan, under the trade name Selvol 205. One suitable example of a polyethylene oxide based adhesive is available from Dow Chemicals Co. located in Midland, Michigan, under the trade name WSR N-80.

If the adhesive is not water-soluble, then water-dispersible adhesives may similarly be utilized. Suitable examples of water dispersible adhesives include thermoplastic elastomer based adhesives and polyvinyl acetate based adhesives. One suitable example of a thermoplastic elastomer based adhesive is available from Actega located in Blue Ash, Ohio, under the trade name Yunico 491. One suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Any suitable pressure sensitive adhesives may be utilized as well. One suitable example of a pressure sensitive adhesives includes sold by Formulated Polymer Products Ltd. Located in Bury, Lancashire, England, and sold under the trade name FP2154. As one specific example, the access seal may comprise a pressure sensitive adhesive.

Without wishing to be bound by theory, it is believed that packages of the present disclosure which utilize adhesives dissolvable in water may comprise a higher weight percentage of such adhesives than adhesives which are only water dispersible. For example, packages comprising water dissolvable adhesives may comprise a first weight percentage of adhesive while packages comprising water dispersible adhesives may comprise a second weight percentage of adhesive. It is believed that the first weight percentage may be greater than the second weight percentage for the purposes of recycling the package material.

Regarding the weight percentage of adhesive allowable and still be recycled is not a uniform standard. For example, adhesives (along with colorants, coatings, and films) are seen as contaminants in the recycling stream. The allowable cumulative weight percentage of each of these is therefore variable. However, in order to meet one of the most stringent recycling standards (disclosed hereinafter), it is believed that the weight percentage of adhesive should not exceed 5 percent by weight of the package material of the package.

That said, it is further believed that where adhesives are utilized which are dissolvable, a higher weight percentage may be utilized as the dissolving adhesive does not negatively impact the recycling process. However, while 5 percent by weight is helpful for the most stringent standard, other jurisdictions may allow up to 50 percent of non-recyclable material or up to 20 percent non-recyclable material. In such jurisdictions, additional adhesive may be utilized if desired. Again, in some forms, the need for adhesive to create the seals described herein may be obviated via the use of a barrier film.

Coatings and Colorants

Each of the plurality of panels comprises an inner surface and an outer surface. The outer surface and/or inner surface of one or more panels may comprise colorants and/or coatings, which create branding on the package, package information, and/or background color, etc. The branding and/or package information can be provided on an outer surface and/or at least a portion of the inner surface, of at least one panel, e.g., the consumer-facing panel. Branding can include logos, trade names, trademarks, icons, and the like, associated with the absorbent articles within the package. Branding can be utilized to inform a consumer of the brand of the absorbent articles within the package. As an example, branding for a package of feminine hygiene pads may comprise the brand name Always®.

Package information can include the size of the absorbent articles, the number of absorbent articles within the package, an exemplary image of the absorbent articles contained within the package, recyclability logos, the like or any combination thereof, associated with the absorbent articles within the package. Additionally, package information can include information regarding the package material itself, e.g., recyclability logos, certifications from various organizations, the like or any combination thereof. As an example, package information for a package of feminine hygiene pads may comprise a size indicator, e.g., "Size 1." Other panels of the package may similarly include branding, package information, and/or background color, along with that associated with the consumer-facing panel.

Additionally, one or more panels of the packages of the present disclosure may comprise colorants and/or coatings, to provide a background color to the packages of the present disclosure. To further clarify the background color, it is worth noting that the packaging material comprises a base color. A base color of the package material is the color of the package material without colorants and/or coatings. For example, bleached package material is white in color, unbleached is brown in color, and package material which includes recycled content is grey in color. A background color is any color that is not a base color, e.g., blue, red, green, yellow, purple, orange, black, or combinations thereof. However, background color can also include white, brown, or grey, if the background color is achieved via colorants and/or coatings.

As noted previously, the use of colorants and/or coatings may be considered to be contaminants in the recyclability stream. So the use of colorants and/or coatings should be carefully reviewed.

In order to reduce the use of colorants and/or coatings, for the benefit of the recycling process, a base color of the package material may be utilized. For example, packages where the consumer-facing panel comprises branding, package information, and/or background color, while one or more panels comprise a base color are contemplated. In one specific example, the bottom panel and/or back panel may utilize the base color of the package material instead of a background color. One or more of the bottom panel, top panel, left panel, right panel, back panel, or any combination thereof may utilize the package material base color instead of a background color. In such examples, the background color may be provided on one or more panels, e.g., consumer-facing panel, while the base color may be utilized on one or more panels. In another example, the consumer-facing panel independently or in conjunction with other panels may be comprise a base color. To further build on this example, the package may comprise absorbent articles which comprise natural-based components, e.g., cotton topsheet and/or non-chlorine bleached pulp in an absorbent core. In such examples, the consumer-facing panel may comprise a base color of white. In this same example, in conjunction with the base color, the consumer-facing panel may further comprise branding, background color (associated with the branding), and/or package information. In still another example, one or more panels may comprise package information, which in part, comprises a base color. To further build on this example, the base color may be a first color, e.g. white, and a background color may be applied to a panel with a negative image of the package information, such that the package information, or a portion thereof, is not covered by the background color, and the package information comprises the first color.

Another method to reduce the use of colorants and/or coatings in the package materials of the present disclosure is to apply variable coverage of colorant and/or coating to a variety of panels. For example, a first panel may comprise a colorant and/or coating percent coverage which is different than a second panel. Further elucidating this example, the consumer-facing panel may have a colorant and/or coating percent coverage which is higher than another panel of the package, e.g., bottom panel. As noted, absorbent articles which are natural based, e.g., cotton topsheets or other components, non-chlorine bleached cores, no added colorants, and/or no added scents, may rely more on the base colors of the package material. As an example, such packages may comprise a consumer-facing panel comprising a colorant coverage of 75 percent or less, more preferably 50 percent or less, or most preferably 40 percent or less. Further the consumer-facing panel may comprise a colorant coverage of from between about 10 percent to about 75 percent, more preferably from about 15 percent to about 50 percent, or most preferably from about 20 percent to about 40 percent, specifically reciting all values within these ranges and any ranges created thereby.

In such packages other panels may be configured having a higher percentage of colorant coverage, lower percentage, or a mix thereof. For example, in such configurations, a bottom panel may comprise a lower percentage of colorant coverage. A back panel, left panel, and/or right panel may comprise a higher percent colorant coverage percentage or more preferably a lower percentage of colorant coverage. These same values may apply for flow wrap configurations and/or stand-up pouch configurations described herein as well.

Natural based products as described are not necessarily limited to the foregoing colorant coverages; however, less colorant percentage can mean less colorant weight percentage which can be beneficial from a recyclability standpoint. In another example, absorbent article packaging in accordance with the present disclosure may comprise a consumer-facing panel having a colorant coverage of 100 percent, more preferably 99 percent or less, or most preferably 98 percent or less. For example, packages in accordance with the present disclosure may comprise a consumer-facing panel having a colorant coverage percentage of from between 60 percent to about 100 percent, more preferably from about 60 percent to about 99 percent, or most preferably from about 60 percent to about 98 percent. In such configurations, other panels may comprise the same percentage of colorant coverage or more preferably may comprise a lower percent of colorant coverage. Colorant coverage percentage is determined via the Percentage of Colorant Coverage Measurement method described herein.

While any suitable colorants may be utilized, the inventors have surprisingly found that water based colorants typically dissolve more readily in water during the recycling process. So, water based colorants can facilitate the recycling process for the packages of the present disclosure. Any suitable water based colorant may be utilized. Water based colorants are well known in the art.

It is worth noting that solvent based colorants and/or energy curable colorants may also be utilized. However, the use of these types of colorants can add complication to the manufacturing of the package material. For example, solvent based colorants generally exhaust volatile organic compounds which are required to be removed from the air. Additionally, solvent based colorants may comprise components which do not readily dissolve in water during the recycling process which could negatively impact the recyclability of the package material.

Energy curable colorants may also be utilized; however, much like the solvent based colorants, energy curable colorants can add complication to the processing of the package material. And much like the solvent based colorants, the energy curable colorants may comprise components which are not readily dissolvable in water during the recycling process which could negatively impact the recyclability of the package material.

Any suitable coating utilized for packaging material may be utilized. Coatings can be utilized to protect the background color, branding, and/or package information. Additionally, coatings may be utilized to provide anti-static benefits, coefficient of friction benefits, and/or appearance benefits, e.g., gloss, matte, satin, high gloss, etc.) Much like water based colorants, the inventors have surprisingly found that water based coatings, if utilized, may facilitate the recycling process of the package material. Suitable coatings comprise varnishes which are well known in the art. Any suitable coating may be utilized.

Figure 2A:
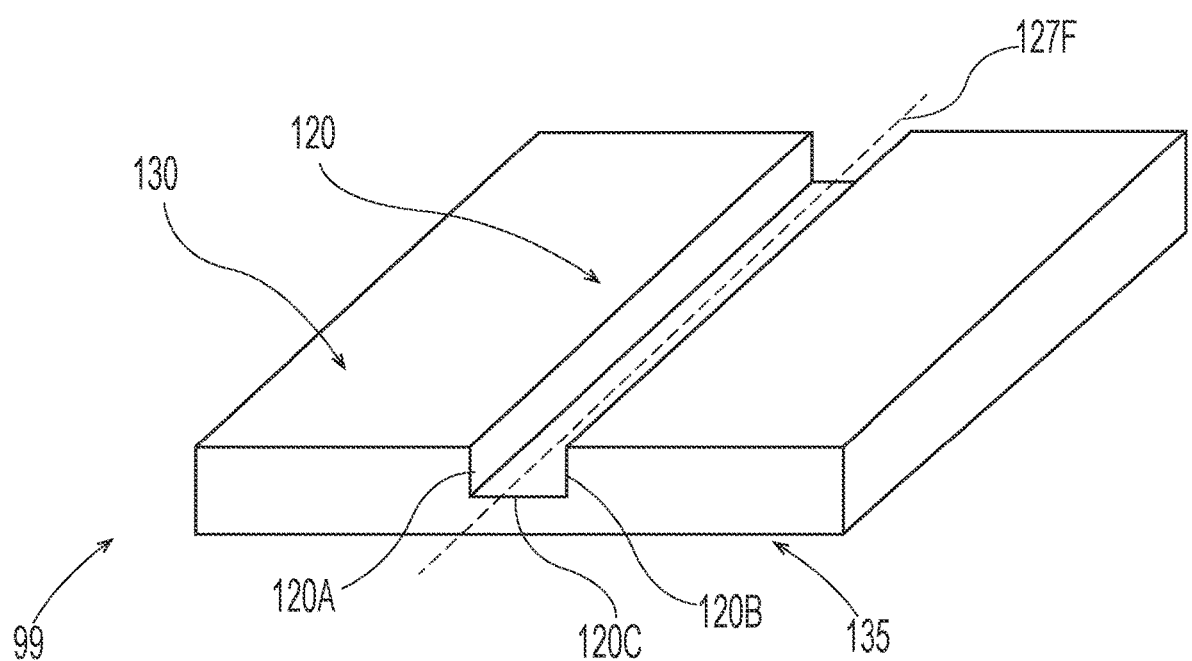
FIG. 2A is a partial cross-sectional view of the package material of FIG. 1 taken along line 2A-2A.

As noted previously, absorbent article manufacturers may purchase the packaging material already preformed into open bags or may purchase rolls of packaging material. Regardless of whether the package material is on rolls or pre-formed to some extent, the packages of the present disclosure begin with paper stock. Referring to FIGS. 1 and 2A, a paper stock sheet 99 may be cut from a web of package material. The paper stock sheet 99 comprises longitudinal side edges 100 and 110 which extend generally in a machine direction (MD). The paper stock sheet 99 further comprises an inner surface 130 and an opposing outer surface 135. Fold lines 127A-127E are shown as dashed lines.

Figure 3:
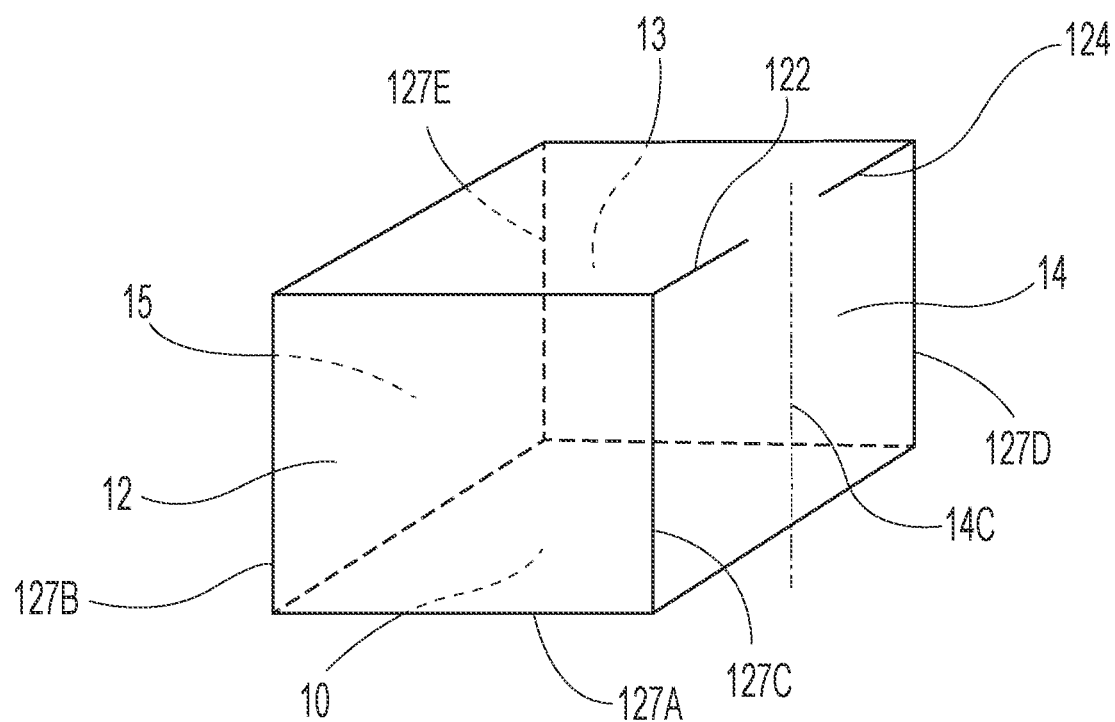
FIG. 3 is a schematic representation of a package in accordance with the present disclosure.

Once folded along the fold lines 127A-127E (the folded configuration of the packages of the present disclosure are shown in FIG. 3 without a top panel 11), these folds can create corners which separate a plurality of panels of the package. For example, as shown, a first fold line 127A can separate a bottom panel 10 from the left panel 12, a consumer-facing panel 14, a right panel 13, and a back panel 15. A cross-wise crease 120 can separate the left panel 12, the consumer-facing panel 14, the right panel 13, and the back panel 15 from the top panel 11.

As discussed previously, the cross-wise crease 120 may extend from one side edge 100 to the opposite side edge 110. Alternatively, the cross-wise crease may comprise a section disposed between the left panel 12 and the top panel 11, between the consumer-facing panel 14 and the top panel 11, between the right panel 13 and the top panel, and/or between the back panel 15 and the top panel 11. Each of these sections comprises a first part and a second part. An example of such construction is shown in FIG. 3. As shown, the cross wise crease 120 comprises a first section disposed between the consumer-facing panel 14 and the top panel 11. The first section comprises a first part 122 and a second part 124. As shown, the first part 122 may extend from an edge formed by the fold line 127C toward a vertical centerline 14C of the consumer-facing panel 14. Similarly, the second section 124 can extend from an opposite edge formed by the fold line 127D toward the vertical centerline 14C of the consumer-facing panel 14. The first part 122 and the second part 124 can be configured as previously described herein.

The remainder of the left panel 12, right panel 13, and/or back panel 15, may comprise sections of the cross-wise crease 120. And, similar to the first section described regarding the consumer-facing panel 14, these other sections also may each comprise a first part and a second part. Referring back to FIG. 1, each of the first parts may extend from their left most fold line, e.g., 127B, toward a vertical centerline of the corresponding panel, i.e., left panel 12. And each of the second parts may extend from their rightmost fold line, e.g., 127C, toward the vertical centerline of the corresponding panel, i.e., left panel 12. The lengths of the fold lines between the top panel and each of the panels listed as being separated therefrom by the cross-wise crease 120, as well as the lengths of the first parts and second parts of the respective sections of the cross-wise crease 120 were discussed previously herein.

Specifically referring to FIG. 2A, the cross-wise crease 120 may comprise a channel which has a bottom surface 120C disposed between the inner surface 130 and the outer surface 135. As shown the channel can extend from the inner surface 130 toward the outer surface 135. In such constructions, sides 120A and 120B of the cross-wise crease 120 may extend from the inner surface 130 toward the outer surface 135. A bottom surface 120C of the cross-wise crease 120 may be disposed between the inner surface 130 and the outer surface 135. As shown, the cross-wise crease 120 is biased from the inner surface 130 toward the outer surface 135.

It is worth noting that the cross-wise crease 120 may be oriented such that it is biased from the outer surface 135 toward the inner surface 130. In such constructions, the cross-wise crease 120 would comprise sides which extend from the outer surface 135 toward the inner surface 130. However, the inventors have found that such constructions where the cross-wise crease 120 is biased from the outer surface 135 toward the inner surface 130 does not function as well as the former configuration. Recall the contrast in data presented in Tables 3 and 4. Table 2 shows that folding in the direction of the crease reduces the forces of folding/recovery as opposed to folding in an opposed direction to the crease.

Figure 2B:
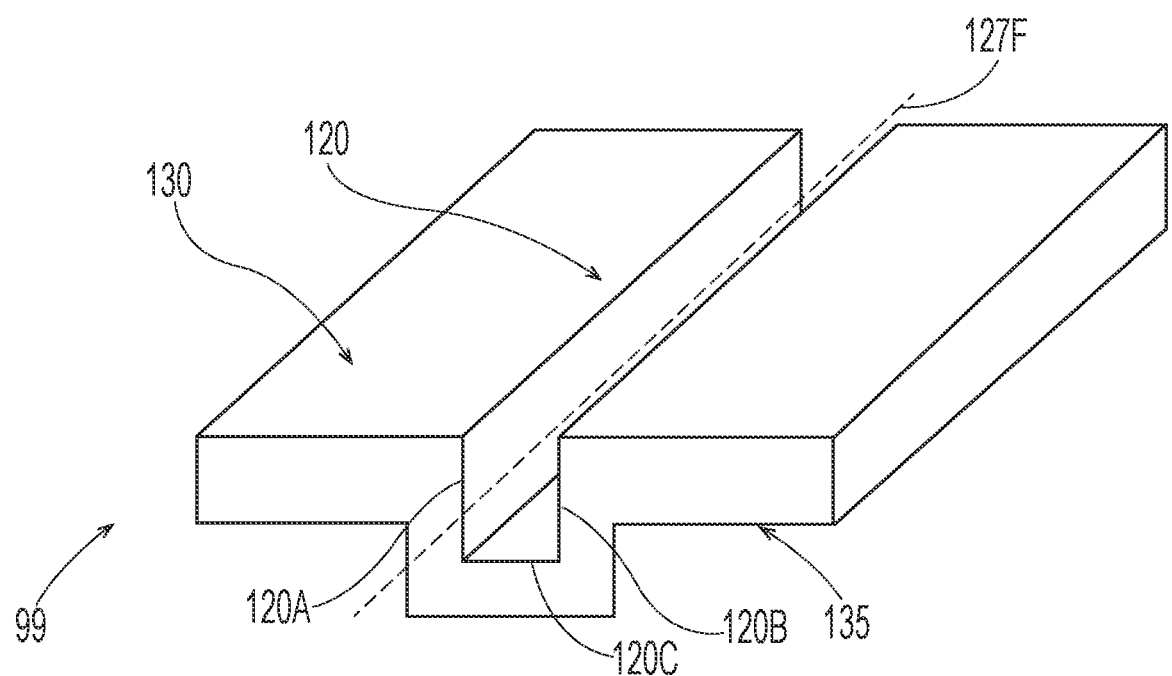
FIG. 2B is a partial cross-sectional view showing an alternative configuration for a crease in accordance with the present disclosure.

It is worth noting that the channel shown in FIG. 2A may comprise a displacement of package material. Referring now to FIG. 2B, the bottom surface 120C may be disposed outboard of the outer surface 135. For example, the cross-wise crease 120 or the bottom surface 120C thereof, may form a discontinuity in the outer surface 135.

Referring now to FIGS. 2A-2B, as noted previously, a top fold line 127F may be colinear with the cross-wise crease 120. The term "colinear" means that a fold line, e.g., top fold line, is generally disposed between sides of the associated crease, e.g., cross-wise crease 120. As shown, the top fold line 127F may be disposed between sides 120A and 120B of the cross-wise crease 120. The sides 120A and 120B may be configured such that the cross-wise crease 120 comprises a "U" shape or a "V" shape. It is worth noting that a "V" shape crease may be preferred over a "U" shape crease for lower caliper materials, e.g., the package material of the present disclosure. In contrast, a "U" shape crease may be beneficial for thicker materials such as cardboard. It is believed that the "V" shape can provide a much more defined fold axis than its "U" shape counterpart.

Figure 4:
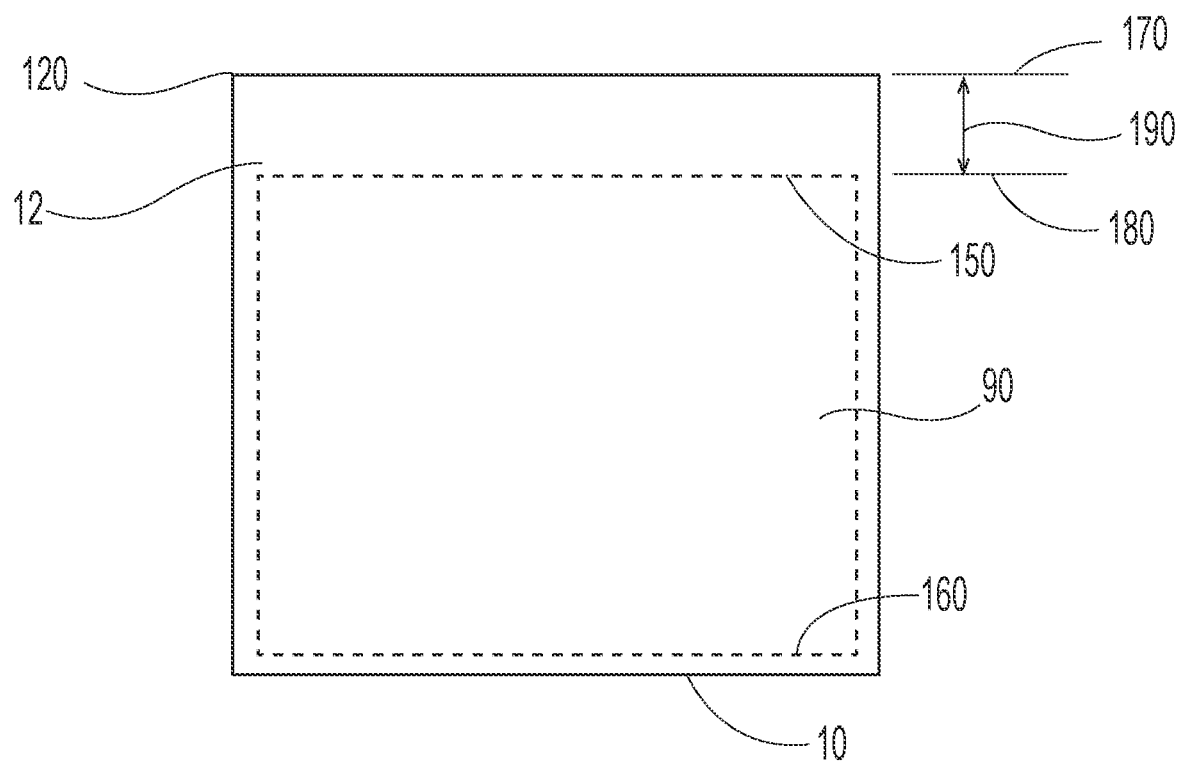
FIG. 4 is a schematic representation of a cross section of a package in accordance with the present disclosure.

Referring now to FIG. 4, a schematic cross section of a package of the present disclosure is shown. An absorbent article 90 may comprise a top edge 150 and a bottom edge 160. The bottom edge 160 is disposed adjacent (as shown, against) the bottom panel 10. And the top edge 150 of the absorbent article 90 is shown adjacent the cross-wise crease 120. A first plane 170 comprising the cross-wise crease 120 and a second plane 180 comprising the top edge 150 may be spaced apart by a distance 190. The distance 190 may be as discussed previously herein. It is worth noting that the first plane 170 comprises substantially all of the cross-wise crease 120 and does not merely intersect it. Similarly, the second plane 180 comprises substantially all of the top edge 150 and does not merely intersect it. Additionally, where the one or more absorbent articles 90 comprise feminine hygiene products which are wrapped, the wrapper should be included as part of the absorbent article 90.

Figure 5A:
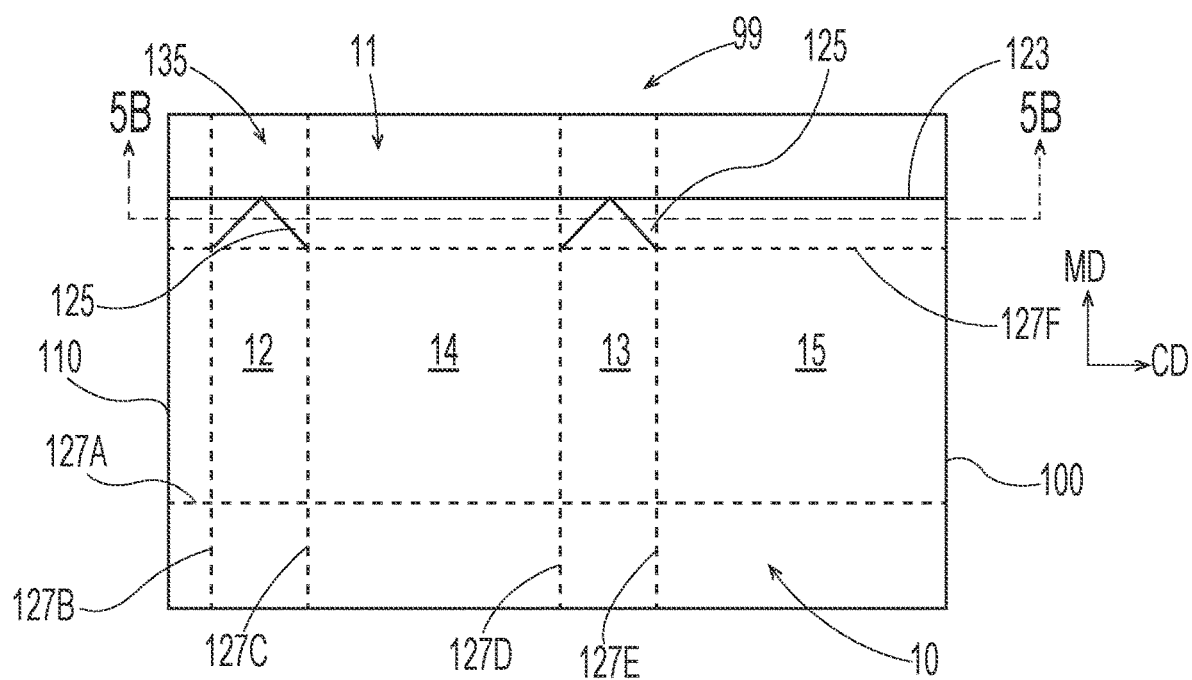
FIG. 5A is a schematic representation showing a web of package material in accordance with the present description showing an outer surface of the package material.
Figure 5B:
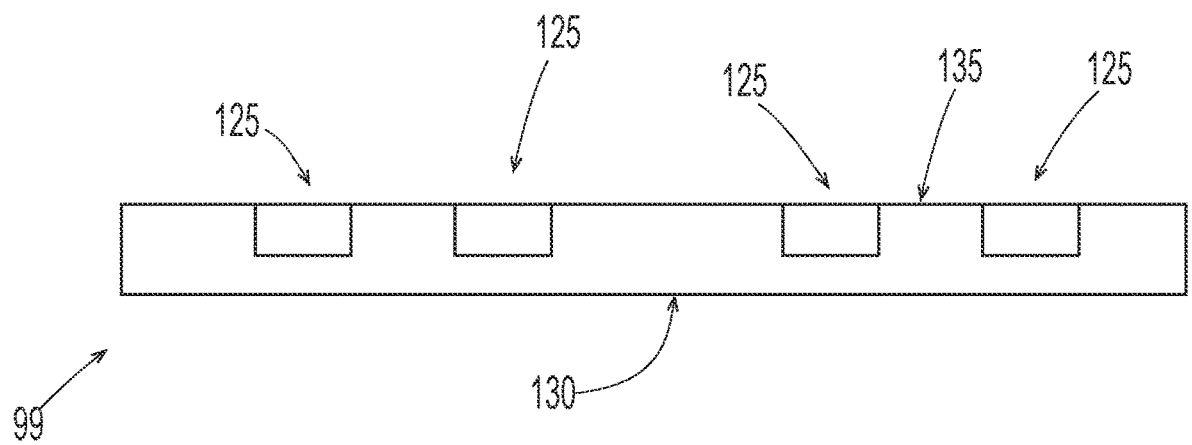
FIG. 5B is a cross-sectional view of the package material of FIG. 5A taken along line 5A-5A.
Figure 5C:
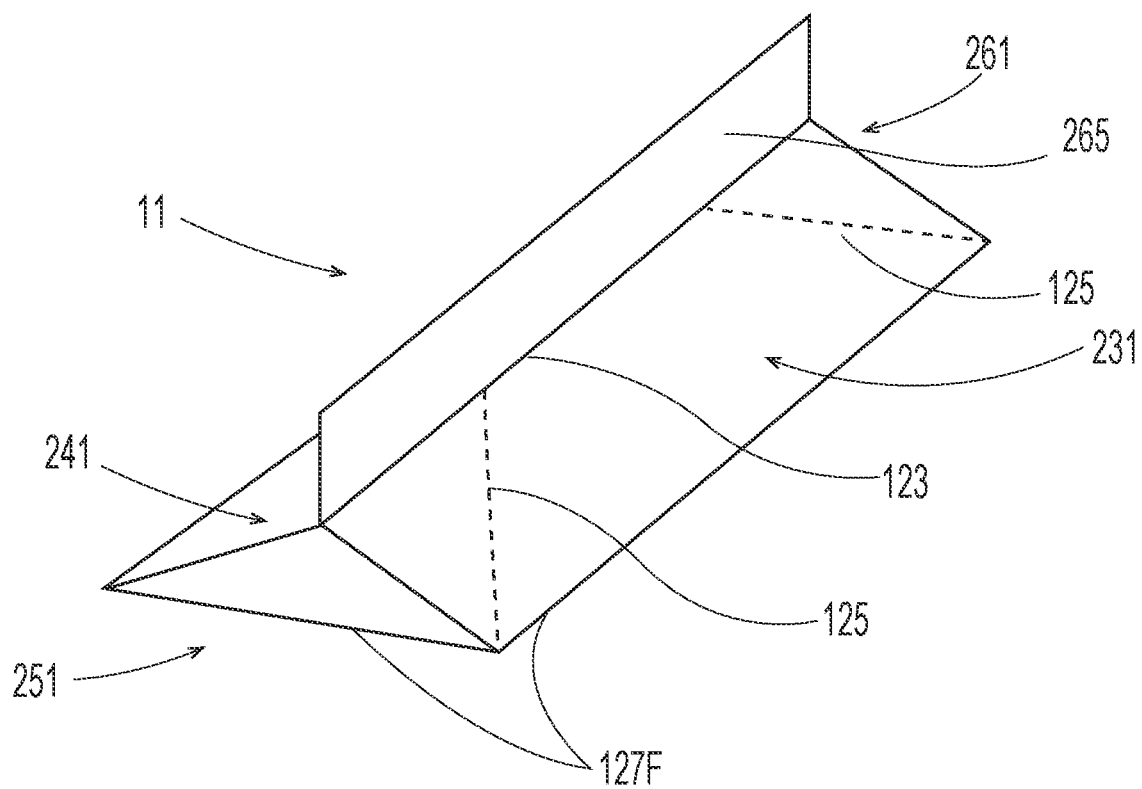
FIG. 5C is a schematic representation showing a top panel of a package of the present disclosure.

Referring now to FIGS. 5A-5C, in FIG. 5A, the outer surface 135 of the package material 99 is shown. Additionally, the package material (web of material) 99 may further comprise gusset creases 125 which correspond to a left face 251 of the top panel 11 and a right face 261 of the top panel 11. As noted previously, the gusset creases 125 can ensure that inner gusset folds, discussed hereinafter are more defined and accurate.

Additionally, the package material 99 may further comprise an opening crease 123. The opening crease 123 may extend from one longitudinal side edge 100 to the other longitudinal side edge 110. Or, the opening crease 123 may be configured as described previously regarding the cross-wise crease 120. For example, the opening crease 123 may be present only on a front face 231 of the top panel 11. The front face 231 may be positioned superjacent to the consumer-facing panel 14. The opening crease 123 may be present only on a back face 241 of the top panel 11. The back face 241 may be positioned superjacent to the back panel 15. However, the inventors have found that when a combination of the front face 231, the left face 251 and the right face 261 include the opening crease 123, that an opening tail 265 can fold toward the back face 241 more easily and provide less recovery force than without the opening crease 123. Lower recovery force in the opening tail 265 can reduce the likelihood that the opening tail 265 kicks off a package which is stacked on top of the opening tail 265.

Alternatively, where folding of the opening tail 265 is desired to be toward the front face 231, the opening crease 123 may be provided on the back face 241, the left face 251 and on the right face 261. And, for the greatest amount of flexibility in which way to fold the opening tail 265, the opening crease 265 may be provided on the front face 231, the back face 251, the left face 251 and the right face 261.

Additionally, where both the front face 231 and back face 251 comprise the opening crease 123, the crease may be oriented differently for each of these faces. For example, the opening crease 123 may comprise a first section on the front face 231 that is oriented from the inner surface toward the outer surface. Namely, the bottom surface of the crease may be recessed from the inner surface, similar to that shown in FIG. 2A or 2B. In contrast, the back face 241 may comprise a third section of the opening crease 123 which is oriented from the outer surface 135 toward the inner surface 130. Or, each of these sections may be oriented in the same direction, e.g., inner surface toward outer surface or outer surface toward inner surface.

Regarding the gusset folds, these are comprised by the left face 251 and the right face 261. Outer gusset folds can be created by fold lines 127B and 127C for the left face 251 and fold lines 127D and 127E for the right face 261. Inner gusset folds are colinear with the gusset creases 125. The inner gusset folds are created during the folding of the packaging material where portions of the material are tucked into the opening tail 265. The gusset creases 125 as shown, may each comprise two legs, one extending toward the consumer-facing panel 14 and the other extending toward the back panel 15.

Specifically referring to FIG. 5B, the gusset creases 125 may be provided as embossed areas of the package material 99. As shown, the gusset creases 125 may be biased from the outer surface 135 toward the inner surface 130. And, although not shown, the opening crease 123 may similarly comprise an embossed area which is biased from the outer surface 135 toward the inner surface 130. The gusset creases 125 and/or the opening crease 123 may be biased from the inner surface 130 toward the outer surface 135; however, the inventor have found such configurations to be not as effective as the former configuration. Additionally, as discussed regarding the cross-wise crease in FIGS. 2A and 2B, the gusset creases 125 and/or the opening crease may comprise a displacement of the package material 99 which provides for a bottom surface of the crease which is outboard of the inner surface 130 or outboard of the outer surface 135 depending on the orientation of these creases.

A variety of package configurations were described previously which could be utilized by an absorbent article manufacturer. These configurations will now be described in additional detail hereafter.

Figure 6:
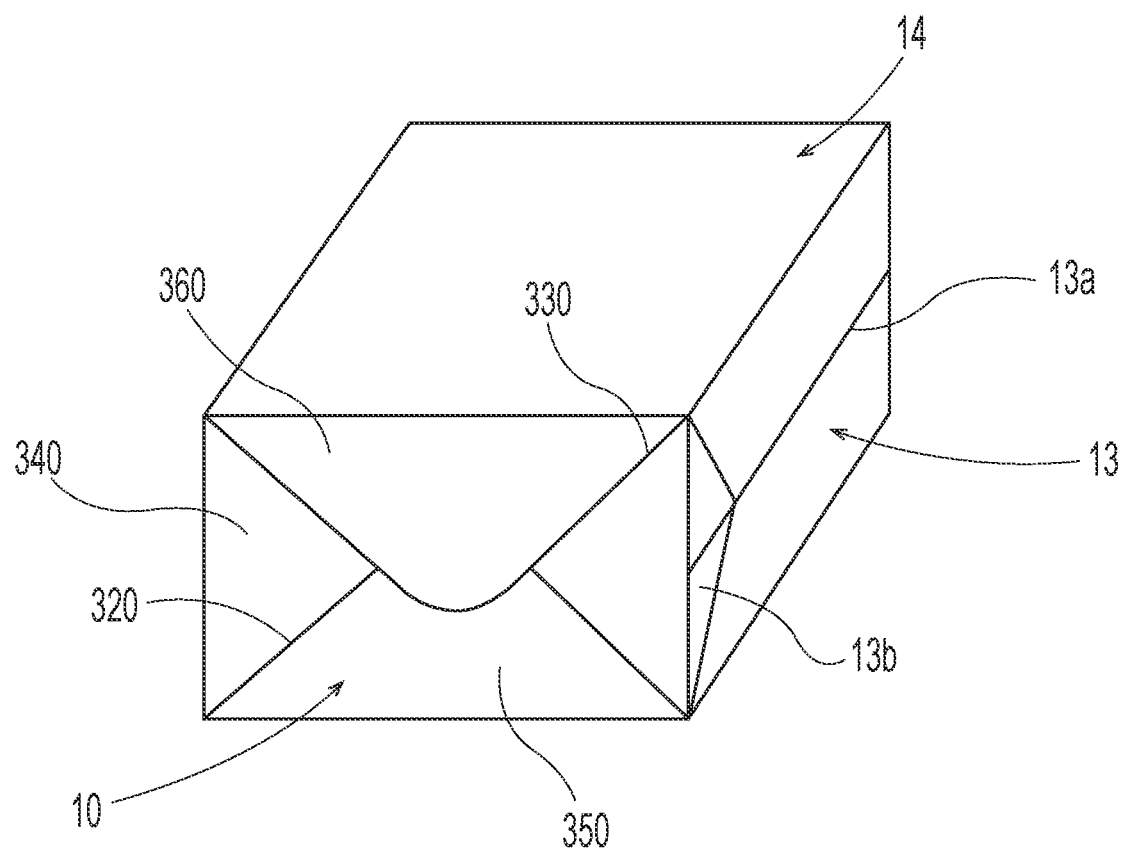
FIG. 6 is a schematic representation of a package of the present disclosure comprises seals in a block bottom style configuration.

An example of a block style configuration is shown in FIG. 6. As shown, the bottom panel 10 may comprise a block style configuration comprising seals 320 and 330. The bottom panel 10 may comprise a base portion 340. A first flap of package material 350 may be folded onto the base portion 340. The first flap of package material 350 may be joined to the base portion 340 thereby forming the first seal 320. A second flap of package material 360 may be folded and joined to the base portion 340 and on top of the first flap of package material 350. And the second flap of package material 360 may be joined to the base portion 340 and to the first flap of package material 350 thereby forming the second seal 330. Recall that adhesive may be used to join these flaps of package material 350 together. Alternatively or in conjunction therewith, for those forms where a barrier film is included, the barrier film may be utilized to create the seals.

Additional panels, e.g., right panel 13 and consumer-facing panel 14 are shown in FIG. 6. As shown, the right panel 13 may comprise a side crease 13a which approximately bisects the right panel 13 and side gussets 13b. Although not shown the left panel 12 similarly may comprise a side crease which approximately bisects the left panel 12 and side gussets.

Referring now to FIGS. 1 and 6, when bags comprising the block bottom configuration are utilized, vertical creases may be provided which correspond to fold lines 127B, 127C, 127D, and 127E. Additionally, block style configurations packages may comprise side creases which approximately bisect the left panel 12 and right panel 13. In some instances with these configurations, creases may also be provided which correspond to fold line 127A. Regarding block style configurations where packages are preformed, i.e., open bags, the absorbent article manufacturer may provide or may request provision of the cross-wise crease 120, the opening crease 123, and/or the gusset creases 125, as described herein.

Figure 7:
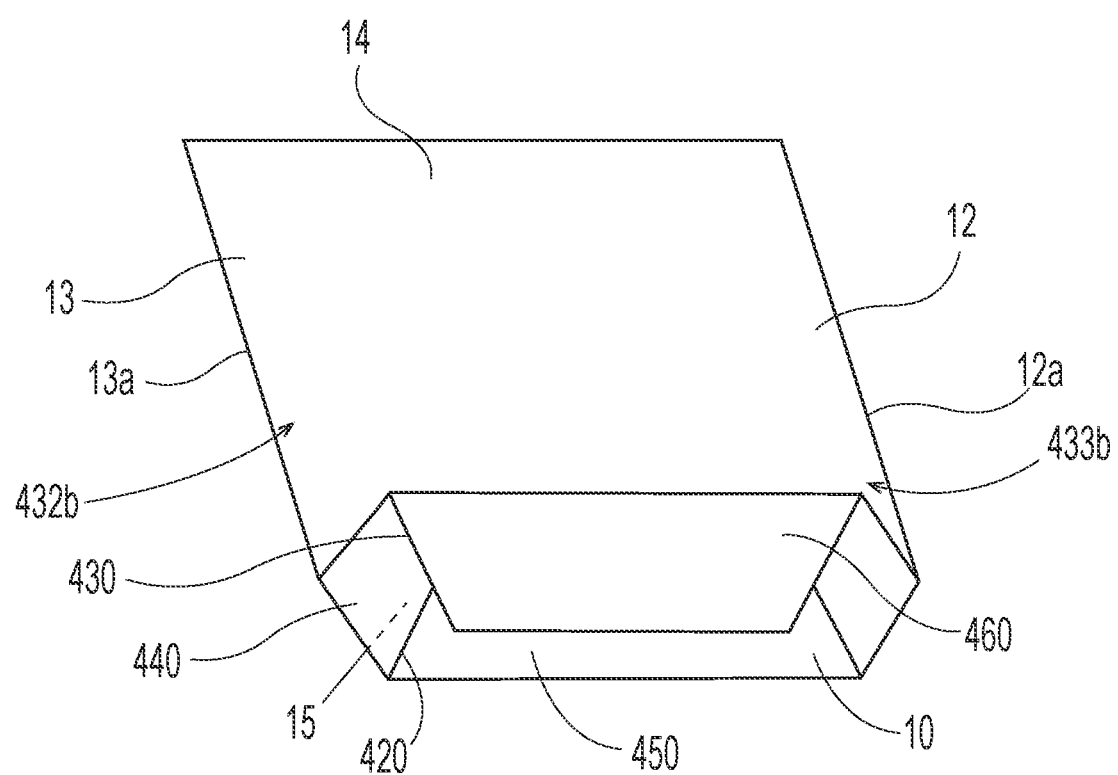
FIG. 7 is a schematic representation of a package of the present disclosure comprises seals in a cross-bottom style configuration.

Cross style configurations are also acceptable for sealing portions of the package material of the present disclosure. An example of a cross bottom style configuration is shown in FIG. 7. As shown, one of the key differences between the cross-style configuration and the block style configuration, is that gussets 432b and 433b as well as side creases 12a and 13a are oriented outward in the cross-style configuration.

Due to the orientation of the gussets 432b and 433b in the cross-style configuration, filling the package with one or more absorbent articles may require less energy to expand the package for filling. As an example, where creases are oriented inward, e.g., block style configuration, would require displacement outward of the creases prior to filling the package. Additionally, the equipment utilized in guiding the product into the package will have a reduced likelihood of interference with the gussets of the cross-style configuration given their orientation outward. This can reduce the likelihood of packaging mishaps or manufacturing process stoppages due to quality issues.

Still referring to FIG. 7, similar to the block style configuration, the bottom panel 10 of the cross-style configuration comprises seals 420 and 430. The bottom panel 10 comprises a base portion 440. A first flap of package material 450 may be folded and joined to the base portion 440. First seal 420 may be provided to attach the first flap of package material 450 to the base portion 440. A second flap of package material 460 may be folded onto the base portion 440 and on top of the first flap of package material 450. Second seal 430 may be provided to join the second flap of package material 460 to the base portion 440 and to the first flap of package material 450. A similar execution may be utilized regarding the top panel (formed after the placement of absorbent articles therein). The joining on these flaps of material may be achieved via adhesive, barrier material or a combination thereof.

Referring now to FIGS. 1 and 7, regarding the cross style configuration, an absorbent article manufacturer may provide or may request the provision of the cross-wise crease 120, the opening crease 123, and the gusset creases 125. However, in addition to the foregoing, the absorbent article manufacturer may additionally provide or request the provision of creases corresponding to fold lines 127B, 127C, 127D, and/or 127E. The provision of these crease lines can provide for corners between adjacent panels and provide for a more premium look to the package. Additionally, the cross-wise crease 120, the opening crease 123, and/or the gusset creases 125, as described herein may be utilized.

Figure 8:
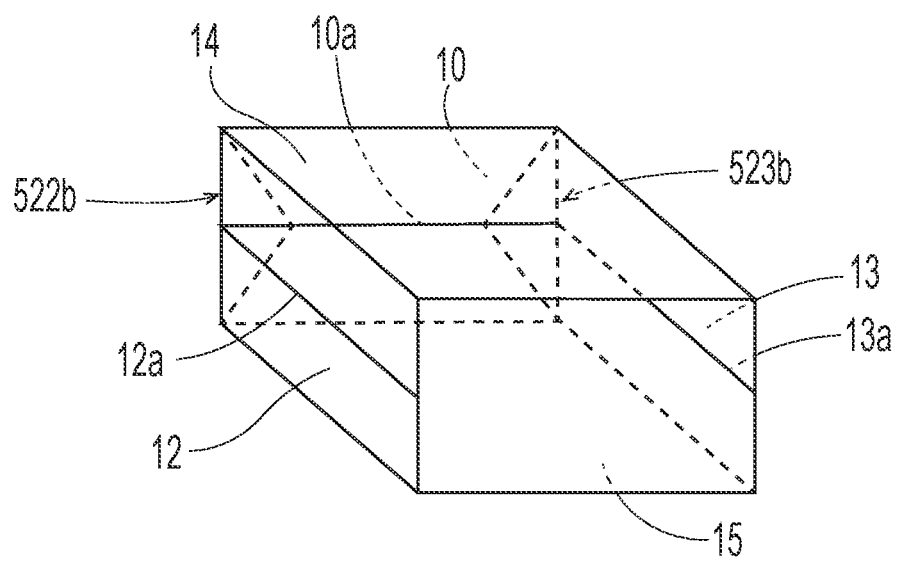
FIG. 8 is a schematic representation showing a package of the present disclosure, wherein the package comprises seals in a pinch bottom configuration.

Still another bag configuration suitable for use as a package in accordance with the present disclosure is a pinch style configuration. An example of a pinch style configuration is shown in FIG. 8. As shown, one of the key differences between the block bottom and the pinch bottom configuration are the crease on the side panels. Instead of creases on the sides 12 and 13, a pinch style configuration comprises gussets 522b and 523b on the bottom panel 10. Additionally, in the pinch bottom configuration, the bottom panel 10 comprises a fold line 10a which may be absent in the block style configuration.

Referring now to FIGS. 1 and 8, similar to the cross-style configuration, where manufacturers utilize a pinch style configuration bag, additional crease may be provided or requested by the manufacturer. For example, the cross-wise crease, the opening crease, the gusset creases, and creases which correspond to fold lines 127B, 127C, 127D, and 127E may be provided.

Figure 9A:
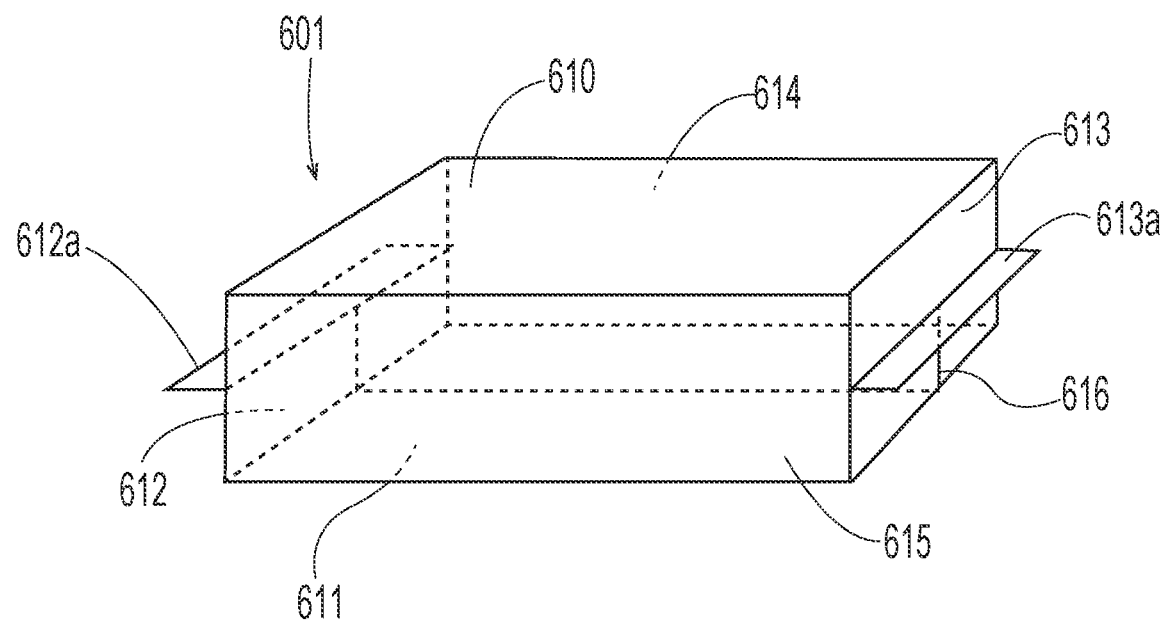
FIG. 9A is a schematic representation showing a package in accordance with the present disclosure constructed with a flow wrap process.
Figure 9B:
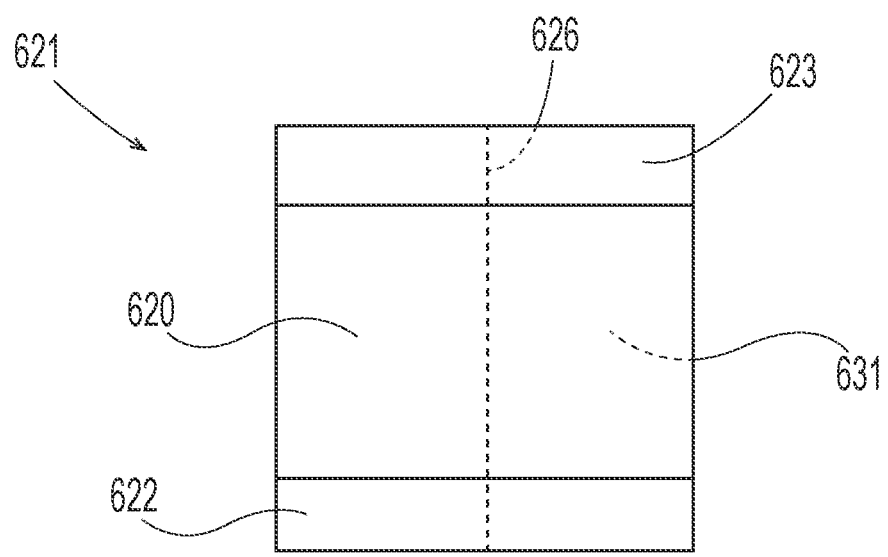
FIG. 9B is a schematic representation showing another package in accordance with the present disclosure constructed with a flow wrap process.

As noted previously, flow wrap package configurations may also be utilized as packaged in accordance with the present disclosure. Some examples of flow wrap packages are shown in FIGS. 9A and 9B. FIG. 9A shows an exemplary flow wrap package which comprises a generally cuboid shape. Package 601, as shown comprises a first panel 610, opposing second and third panel 612 and 613, respectively; opposing fourth and fifth panel 614 and 615, respectively, and a sixth panel 611 opposing the first panel 610. As shown, the second panel 612 may comprise an end seal 612a, and the third panel 613 may comprise an end seal 613a. A hoop seal 616 may be disposed, in part on the second panel 612, the third panel 613, and the sixth panel 611. In such configurations, either the first panel 610 or the fifth panel 615 may comprise the consumer-facing panel.

FIG. 9B shows another exemplary package 621 in accordance with the packages of the present disclosure. Much like package 601 of FIG. 9A, package 621 is a flow wrap configuration. As shown, package 621 comprises a first surface 620 and an opposing second surface 631. Rounded edges may be provided as a transition between the first surface 620 and the second surface 631. Or, one or more fold lines may be provided between the first surface 620 and the second surface 631. Package 621 may further comprise end seals 622 and 623, and a hoop seal 626 which may be disposed on the second surface 631. In such packages, the first surface 620 may comprise the consumer-facing panel.

Regarding both FIGS. 9A and 9B, while the packages shown, i.e., 601 and 621, comprise butt seals for the end seal, overlap seals may also be utilized. For example, one or more of the end seals 612a, 613a, 622, and 623 may comprise an overlap seal. Similarly, the hoop seal, i.e., 616 and 626, may comprise either a butt seal or an overlap seal.

As noted previously, flow wrap packaging does not comprise pre-formed packages. So, manufacturers utilizing such configurations typically produce such packaging from a web of material. Utilizing such configurations, manufacturers of absorbent articles may provide creases such as the cross-wise crease, the opening crease, the gusset creases, and creases which correspond to fold lines 127B, 127C, 127D, and 127E (shown in FIG. 1).

Figure 10A:
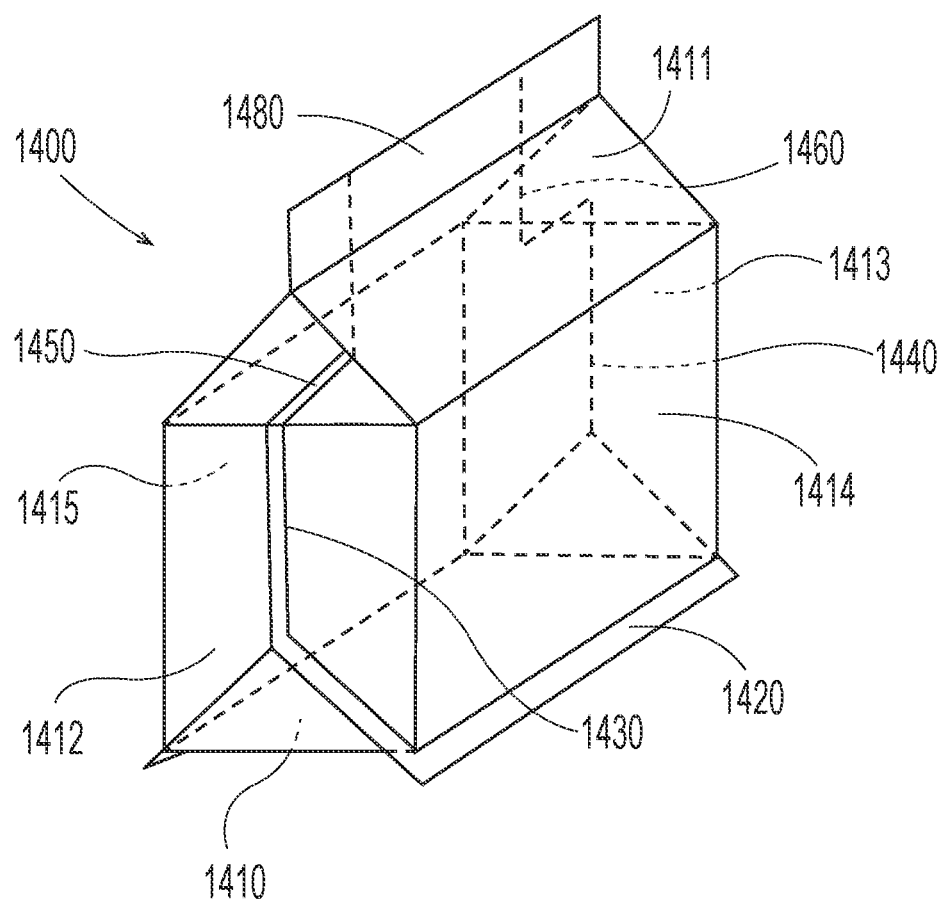
FIG. 10A is a schematic representation showing another package in accordance with the present disclosure constructed in accordance with the present disclosure.
Figure 10B:
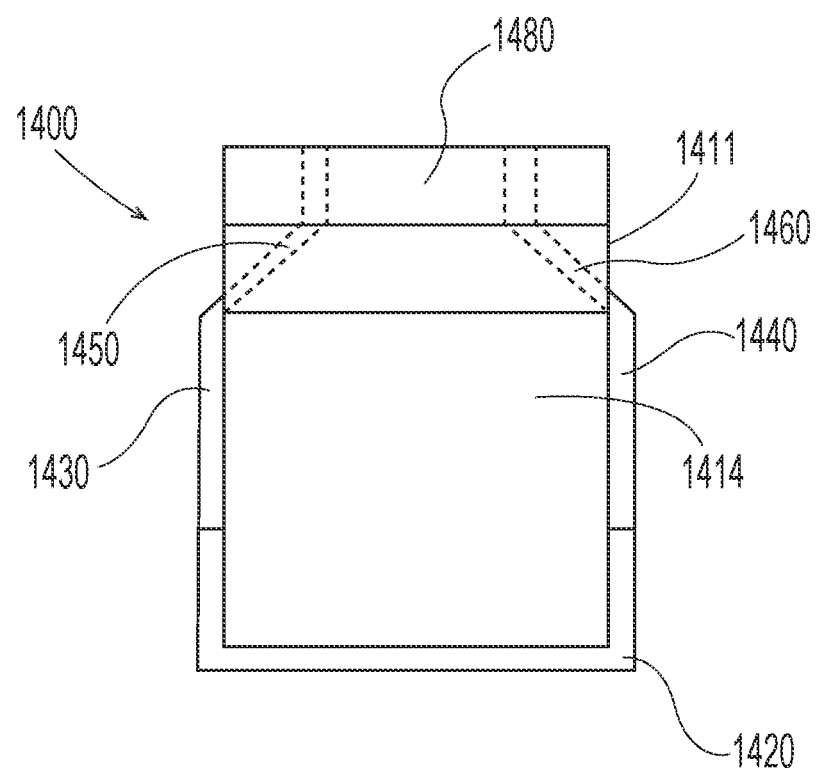
FIG. 10B is a schematic representation showing a rotated view of the package of FIG. 10A.

In yet another example, a stand-up pouch style bag may be utilized. The stand-up pouch style of bag may comprise seams/seals which are more overt than their block bottom, pinch bottom, and/or cross bottom counterparts. Referring to FIGS. 10A and 10B, a stand-up pouch style package 1400 is shown. The package 1400 may be configured in generally a cuboid shape. The package 1400 may comprise a first panel 1411, opposing second and third panels 1412 and 1413, opposing fourth and fifth panels 1414 and 1415, and a sixth panel 1410 opposing the first panel 1411. As shown, between the fourth panel 1414 and the sixth panel 1410, a first seal 1420 may extend outward. The first seal 1420 forms a sort of foot for the package 1400. A second seal may extend outward between the fifth panel 1415 and the sixth panel 1410 in a similar fashion to the first seal 1420. It is worth noting that in some forms, the first panel 1411 may lay flat much like the sixth panel 1410.

The first seal 1420 can extend such that a portion of the first seal 1420 is on the second panel 1412 and another portion of the first seal 1420 is disposed on the third panel 1413. Similarly, a portion of the second seal may be disposed on the second panel 1412 and another portion may be disposed on the third panel 1413. The first seal 1420 and the second seal may be provided where the sixth panel 1410 is formed from a discrete piece of material which is subsequently joined to the fourth panel 1414 and fifth panel 1415. Of course forms where the sixth panel 1410 is unitary with the fourth panel 1414 and fifth panel 1415 are also contemplated.

A third seal 1430 and a fourth seal 1440 may extend outward from the second panel 1412 and the third panel 1413, respectively. It is worth noting that the first seal 1420, second seal, third seal 1430, and fourth seal 1440 collectively may comprise the hoop seal discussed heretofore. So one, all or any combination, of these seals may exhibit the tensile strength for the hoop seal as described herein.

As shown, the package 1400 may further comprise a fifth seam 1450 and a sixth seam 1460 which are disposed on the sixth panel 1411. The fifth seam 1450 and sixth seam 1460 can extend into a seal fin 1480. It is worth noting that the package 1400 and the seams associated therewith, may be assembled as described herein regarding adhesives, films, and/or combinations of films and adhesives. However, the construction of the package 1400 is particularly well suited for the creation of seams via film coating on an inner surface of the package material. In such configurations, the film may form a barrier that reduces the likelihood or at least the amount of moisture vapor through the package material to the absorbent articles therein.

For the stand-up pouch style configuration, the provision of creases, e.g., cross-wise crease, opening crease, the gusset creases, and creases which correspond to fold lines 127B, 127C, 127D, and 127E (shown in FIG. 1) may be utilized.

Figure 11:
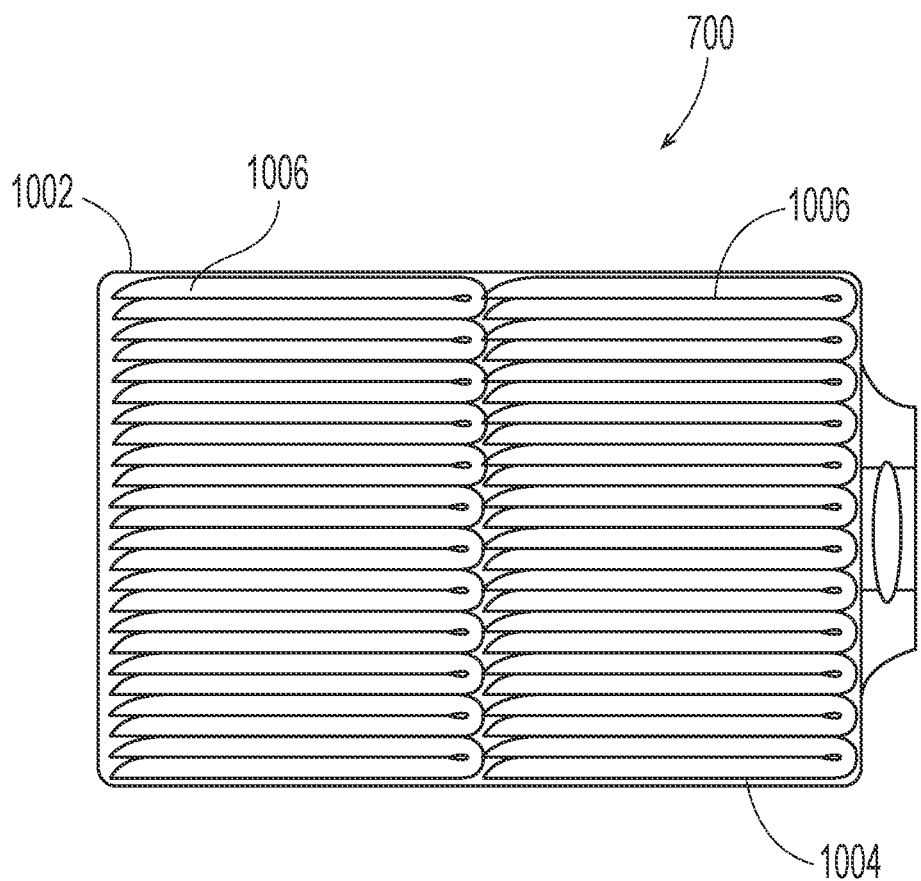
FIG. 11 is a cross-sectional view of a package in accordance with the present disclosure showing absorbent articles therein.

Regardless of the package configuration, the package may comprise a plurality of compressed articles, e.g., compressed disposable absorbent articles. For example, the package 700 of the present disclosure may be used for accommodating feminine hygiene pads. As shown in FIG. 11, the package 700 defines an interior space 1002 in which a plurality of absorbent articles 1004 are situated. The plurality of absorbent articles 1004 may be arranged in one or more stacks 1006. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. Despite lacking the stretch properties of conventional plastic packaging material, the inventors have surprisingly found the package materials of the present disclosure are able to withstand the processing and distribution rigors, as mentioned heretofore, even with absorbent articles which are compressed within the package. This is particularly unexpected as the materials of the present invention do not display the stretch properties of presently used conventional plastic films.

Accordingly, packages of the absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

It is worth noting that the absorbent articles within the packages of the present disclosure can be arranged in a myriad of configurations. For example, absorbent articles of the present disclosure may be disposed within the package such that they are oriented in a vertical orientation, or the absorbent articles may be arranged such that they are arranged in a horizontal configuration, for example as shown in FIG. 6. Forms are contemplated where a combination of horizontal and vertically oriented articles are provided in the package.

Additionally, the articles within the package may be oriented such that one longitudinal peripheral edge of each of the plurality of articles is more proximal to the consumer-facing panel than another longitudinal peripheral edge. For example, where the number of absorbent articles within the package is relatively high, e.g., greater than nine, the absorbent articles may be arranged within the package as described heretofore. However, where the number of absorbent articles within the package is lower than, for example nine, the absorbent articles may be arranged such that a topsheet or a backsheet of an absorbent article is more proximal to the consumer-facing panel. Additional absorbent articles may be stacked behind the absorbent article which is closest to the consumer-facing panel. Forms are contemplated where there is a combination of orientations within the package. For example, at least one absorbent article can be arranged such that one of its longitudinal peripheral side edges is more proximal the consumer-facing panel than another, and at least one absorbent article can be arranged such that its topsheet or backsheet is more proximal to the consumer-facing panel. The remainder of the absorbent articles, if any, can assume either of those configurations.

Absorbent Articles

Figure 12:
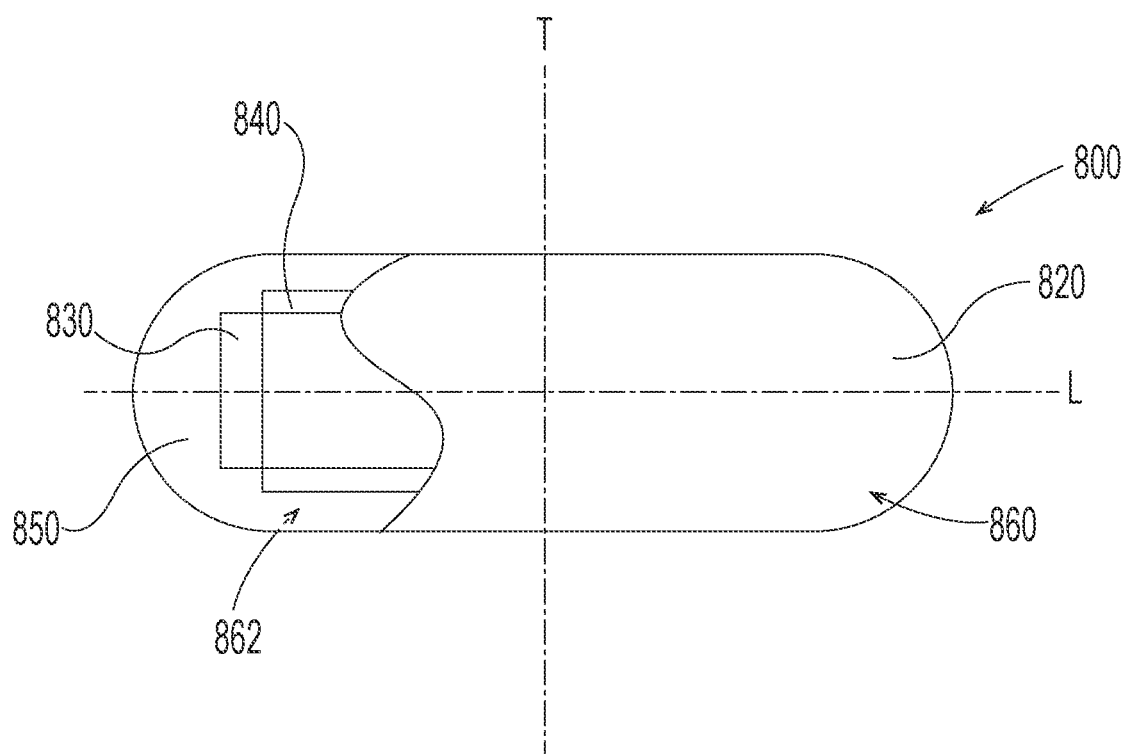
FIG. 12 is a schematic representation of an absorbent article of the present disclosure showing a partial-cutaway-view of the article.
Figure 13A:
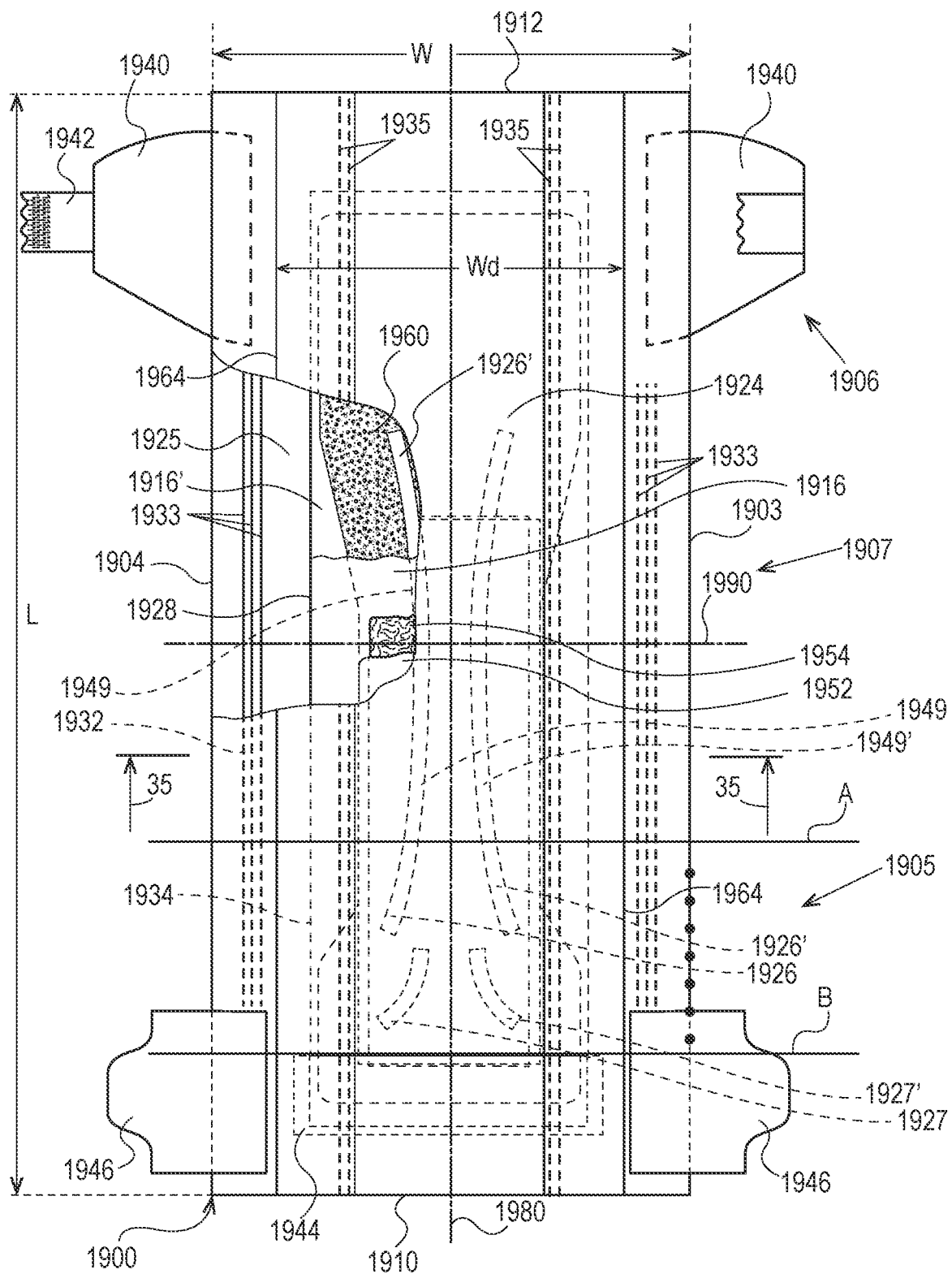
FIG. 13A shows a plan view of a diaper constructed in accordance with the present disclosure.
Figure 13B:
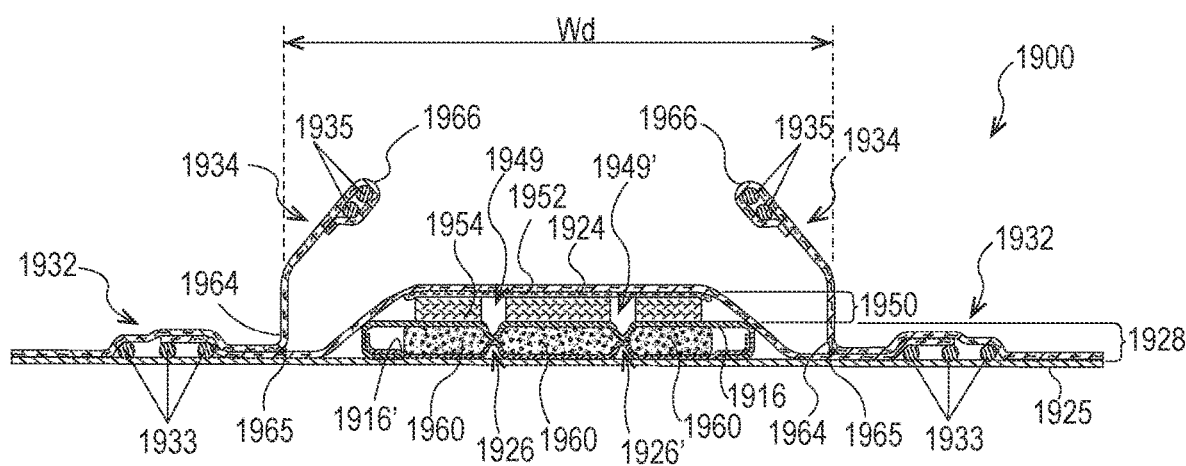
FIG. 13B shows a cross section of the diaper of FIG. 13A taken along lines 35-35.
Figure 13C:
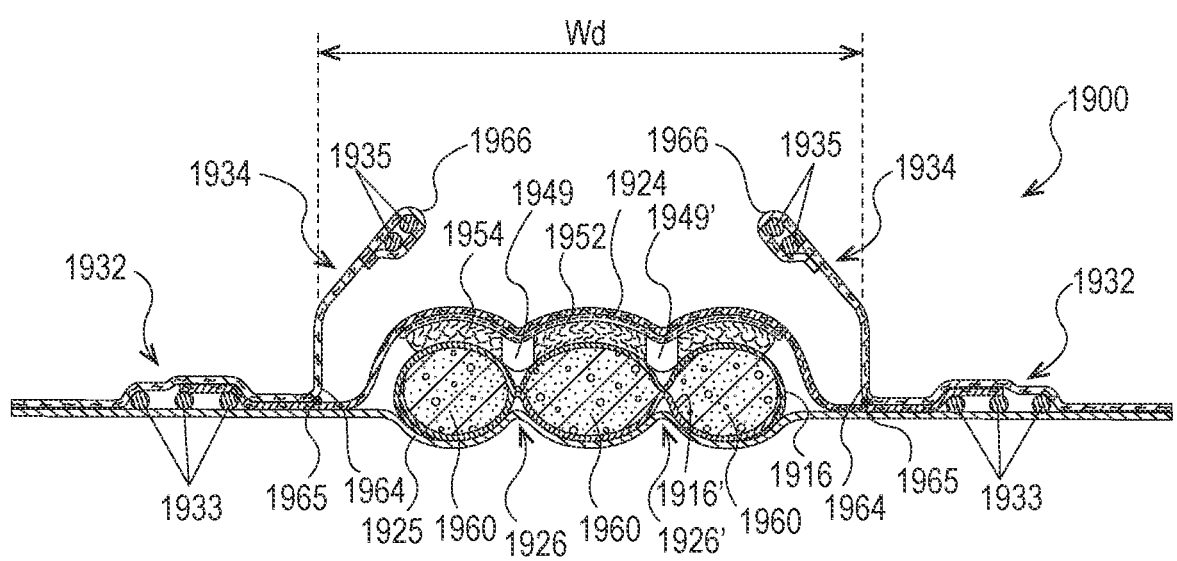
FIG. 13C shows a cross section of the diaper of FIG. 13B in an expanded state.

As noted previously, the absorbent articles which can be packaged within the package material of the present disclosure are numerous. Two specific examples are provided in FIGS. 12 through 13C. However, the package material and packages of the present disclosure may be utilized to contain a multitude of absorbent articles as described previously. FIGS. 12 through 13C are merely examples of articles which may be contained with the package material/packages of the present disclosure.

In FIG. 12 an exemplary feminine hygiene pad 800 is shown. The feminine hygiene pad 800 comprises a topsheet 820, a backsheet 850, and an absorbent core 840 disposed between the topsheet 820 and the backsheet 850. A fluid management layer 830 may be disposed between the topsheet 820 and the absorbent core 840. The absorbent article has a wearer-facing surface 860 and an opposing garment-facing surface 862. The wearer-facing surface 860 primarily comprises the topsheet 820 while the garment-facing surface 862 primarily comprises the backsheet 850. Additional components may be included in either the wearer-facing surface 860 and/or the garment-facing surface 862. For example, where the absorbent article is an incontinence pad, a pair of barrier cuffs which extend generally parallel to a longitudinal axis L of the absorbent article 800, may also form a portion of the wearer-facing surface 860. Similarly, a fastening adhesive may be present on the backsheet 450 and form a portion of the garment-facing surface 862 of the absorbent article.

The topsheet 820 may be joined to the backsheet 850 by attachment methods (not shown) such as those well known in the art. The topsheet 820 and the backsheet 850 may be joined directly to each other in the article periphery and may be indirectly joined together by directly joining them to the absorbent core 840, the fluid management layer 830, and/or additional layers disposed between the topsheet 820 and the backsheet 850. This indirect or direct joining may be accomplished by attachment methods which are well known in the art.

The topsheet 820 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 820 can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet include fibrous materials made from natural fibers, e.g., cotton, including 100 percent organic cotton, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, using any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 820 may be formed from a combination of an apertured film and a nonwoven. For example, a film web and a nonwoven web can be combined as described in U.S. Pat. No. 9,700,463. Alternatively, a film may be extruded onto a nonwoven material which is believed to provide enhanced contact between the film layer and the nonwoven material. Exemplary processes for such a combination are described in U.S. Pat. Nos. 9,849,602 and 9,700,463.

The backsheet 850 may be positioned adjacent a garment-facing surface of the absorbent core 840 and may be joined thereto by attachment methods such as those well known in the art. For example, the backsheet 850 may be secured to the absorbent core 840 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 850 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet may prevent, or at least inhibit, the exudates absorbed and contained in the absorbent core from wetting articles of clothing which contact the incontinence pad such as undergarments. However, the backsheet may permit vapors to escape from the absorbent core (i.e., is breathable) while in some cases the backsheet may not permit vapors to escape (i.e., non-breathable). Thus, the backsheet may comprise a polymeric film such as thermoplastic films of polyethylene or polypropylene. A suitable material for the backsheet is a thermoplastic film having a thickness of from about 0.012 mm (0.5 mil) to about 0.051 mm (2.0 mils), for example. Any suitable backsheet known in the art may be utilized with the present invention.

The backsheet 850 acts as a barrier to any absorbed bodily fluids that may pass through the absorbent core 840 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Exemplary backsheets are described in U.S. Pat. No. 5,885,265 (Osborn, III.) issued Mar. 23, 1999; U.S. Pat. No. 6,462,251 (Cimini) issued Oct. 8, 2002; U.S. Pat. No. 6,623,464 (Bewick-Sonntag) issued Sep. 23, 2003, or U.S. Pat. No. 6,664,439 (Arndt) issued Dec. 16, 2003. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242, and WO 97/24097.

The backsheet may be a nonwoven web having a basis weight between about 20 gsm and about 50 gsm. As an example, the backsheet can be a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

The absorbent core 840 may comprise any suitable shape including but not limited to an oval, a discorectangle, a rectangle, an asymmetric shape, and an hourglass. For example, in some forms of the present invention, the absorbent core 440 may comprise a contoured shape, e.g., narrower in the intermediate region than in the end regions. As yet another example, the absorbent core may comprise a tapered shape having a wider portion in one end region of the pad which tapers to a narrower end region in the other end region of the pad. The absorbent core may comprise varying stiffness in the MD and CD.

The configuration and construction of the absorbent core may vary (e.g., the absorbent core 840 may have varying caliper zones, a hydrophilic gradient, a superabsorbent gradient, or lower average density and lower average basis weight acquisition zones). Further, the size and absorbent capacity of the absorbent core 840 may also be varied to accommodate a variety of wearers. However, the total absorbent capacity of the absorbent core 840 should be compatible with the design loading and the intended use of the disposable absorbent article or incontinence pad.

In some forms of the present invention, the absorbent core may comprise a plurality of multi-functional layers that are in addition to the first and second laminates. For example, the absorbent core may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself. The absorbent core may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the core of the present disclosure are envisioned. In particular, potential additions to the current multi-laminate absorbent core are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described laminates of the absorbent core of the present invention. Additional examples of suitable absorbent cores are described in U.S. Patent Application Publication Nos. 2018/0098893 and 2018/0098891.

Any suitable fluid management layer may be utilized in conjunction with the feminine hygiene pad 800. The fluid management layer may be separate and apart from the absorbent system. Additionally, the fluid management layer is disposed beneath the topsheet and on the wearer-facing surface of the core. The fluid management layer may have a basis weight from about 40 gsm to about 100 gsm, from about 45 gsm to about 75 gsm, or from about 50 gsm to about 65 gsm, specifically including all values within these ranges and any ranges created thereby. In some forms, the fluid management layer may comprise a homogeneous mix of fibers whereas in other forms, the fluid management layer may comprise a heterogeneous mix of fibers.

Some exemplary fluid management layers are described in U.S. Patent Application Publication Nos. 2015/0351976 A1 and 2014/0343523 A1; and U.S. patent application Ser. No. 15/729,704.

Another example of an absorbent article which can be included in the packages of the present disclosure are diapers. As shown in FIG. 13A, a plan view of an example absorbent article 1900 that is a diaper in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the packages of the present disclosure may be used for a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 13B), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone 1944 on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge

1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 13A. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 1916 and 1916' for the top side and bottom side of the core.

The absorbent core 1928 may comprises one or more channels, represented in FIG. 13A as the four channels 1926, 1926' and 1927, 1927'. Additionally or alternative, the LMS 1950 may comprises one or more channels, represented in FIGS. 13A-13C as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm Example backsheet films include those manufactured by Tredegar Corporation, based in Richmond, VA, and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, non-woven webs, and composite materials such as film-coated nonwoven webs, microporous films, and monolithic films.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above.

This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 5A. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer of absorbent material, which may be 100% or less of SAP. The second absorbent layer may comprise the second material 1916' and a second layer of absorbent material, which may also be 100% or less of SAP.

A fibrous thermoplastic adhesive material may be at least partially in contact with the absorbent material 1960 in the land areas and at least partially in contact with the materials 1916 and 1916' in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal for the core wrap does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article may comprise a pair of barrier leg cuffs 1934 and leg gather elastics 1933. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 1964 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal. It is worth noting that barrier leg cuffs may similarly be applied to a pad type of structure as described regarding FIG. 12. Such configurations may be desirable in an adult incontinence pad. Any of the configurations described herein for the barrier leg cuffs may be utilized for adult incontinence pads.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 13A, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise two layers: a distribution layer 1954 and an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Grad), for example.

The LMS 1950 may comprise a distribution layer 1954. The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 1950 may alternatively or additionally comprise an acquisition layer 1952. The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Arrays of Packages

With the package material of the present disclosure, it is contemplated that a wide variety of packaging arrays may be provided to address the concerns of a variety of consumers. As an example, the packages of the present disclosure may be utilized with absorbent articles which have more components which are natural or have natural components. For example, the packages of the present disclosure may be utilized with absorbent articles which include a cotton topsheet and/or a cotton based fluid management layer or acquisition layer. Additionally or alternatively, the packages of the present disclosure can be utilized with absorbent articles which are unscented and/or have unbleached pulp in their absorbent cores.

While some of the absorbent article offerings may be in the packages of the present disclosure, other of the absorbent article offerings may be in conventional packaging. However, in an effort to drive more sustainable manufacturing practices, it is contemplated of the absorbent articles offered by a single manufacturer of absorbent articles on a store shelf, that at least 20 percent comprise recyclable packages as described herein, more preferably at least 40 percent, or most preferably at least 50 percent, specifically reciting all values within these ranges or any ranges created thereby. For example, where a manufacturer of absorbent articles has 5 absorbent article offerings on a store shelf, e.g., 2 diapers sizes, 3 feminine hygiene pad sizes, at least one of the packages for a single diaper size or a single feminine hygiene pads size may comprise recyclable packaging as described herein.

Arrays are contemplated where the package material of the present disclosure is utilized for two different absorbent articles and wherein the packages have a different seal configuration. For example, a first package may comprise a plurality of feminine hygiene pads and comprise at least one panel having a block style configuration. A second package may comprise a plurality of diapers and comprise at least one panel having a pinch style or cross style configuration.

Contemplated Examples

Example A. A package of one or more absorbent articles, wherein the one or more absorbent articles are sealed within the package, the package comprising: a plurality of panels, including a consumer-facing panel and a top panel disposed superjacent to the consumer-facing panel, wherein each of the plurality of panels comprises an inner surface and an outer surface; a top fold line disposed between the consumer-facing panel and the top panel, wherein the top fold line is colinear, at least in part, with a cross-wise crease; wherein the package material comprises natural fibers and wherein the cross-wise crease exhibits a Peak Load of about 1.8 N or less, more preferably about 1.7 N or less.

Example A1. The package of any of Example A, wherein the top panel comprises a front face, an opposing back face, a right face and an opposing left face and an opening tail.

Example A2. The package of Example A1, wherein at least one of the front face and/or the back face comprise an opening crease.

Example A3. The package of any of Examples A1 or A2, wherein the right face and/or the left face comprise gusset creases.

Example A4. The package of any of Examples A-A3, wherein the package further comprises a back panel opposed to the consumer-facing panel, a left panel disposed between the consumer-facing panel and the back panel, and a right panel disposed between the consumer-facing panel and the back panel.

Example A5. The package of Example 4 further comprising one or more vertical creases disposed between the consumer-facing panel and the left panel, the consumer-facing panel and the right panel, the right panel and the back panel, and/or the left panel and the back panel.

Example A6. The package of any of Examples A-A5, wherein the cross-wise crease is disposed in a first plane and a top edge of the one or more absorbent articles is disposed in a second plane, and wherein a distance between the first plane and the second plane is about 5 mm or less, more preferably about 3 mm or less, or most preferably about 2 mm or less.

Example A7. The package of any of Examples A-A6, wherein the cross-wise crease has a depth of greater than about 0.01 mm, more preferably greater than about 0.02 mm, or most preferably greater than about 0.03 mm.

Example A8. The package of any of Examples A-A7, wherein the cross-wise crease has a depth of from about 0.01 mm to about 0.9 mm, more preferably from about 0.02 mm to about 0.7, or most preferably from about 0.03 mm to about 0.5 mm.

Example A9. The package of any of Examples A2-A8, wherein the opening crease has a depth of greater than about 0.01 mm, more preferably greater than about 0.02 mm, or most preferably greater than about 0.03 mm.

Example A10. The package of any of Examples A2-A9, wherein the opening crease has a depth of from about 0.01 mm to about 0.9 mm, more preferably from about 0.02 mm to about 0.7, or most preferably from about 0.03 mm to about 0.5 mm.

Example A11. The package of any of Examples A-A10, wherein the cross-wise crease has a width of from about 0.1 mm to about 7 mm, more preferably from about 0.1 mm to about 5 mm or most preferably from about 0.1 mm to about 4 mm.

Example A12. The package of any of Examples A-A11, wherein the cross-wise crease has a width of from about 0.1 mm to about 3 mm, more preferably from about 0.1 mm to about 2 mm, or most preferably from about 0.1 mm to about 1 mm.

Example A13. The package of any of Examples A2-A12, wherein the opening crease has a width of from about 0.1 mm to about 7 mm, more preferably from about 0.1 mm to about 5 mm or most preferably from about 0.1 mm to about 4 mm.

Example A14. The package of any of Examples A2-A13, wherein the opening crease has a width of from about 0.1 mm to about 3 mm, more preferably from about 0.1 mm to about 2 mm, or most preferably from about 0.1 mm to about 1 mm.

Example A15. The package of any of Examples A-A14, wherein the cross-wise crease is biased from the inner surface toward the outer surface.

Example A16. The package of any of Examples A2-A15, wherein the opening crease is biased from the inner surface toward the outer surface.

Example A17. The package of Example A16, wherein the opening crease is disposed on the front face.

Example A18. The package of any of Examples A-A17, wherein the cross-wise crease exhibits a Peak Load of from about 0.7 N to about 1.8 N or more preferably from about 0.8 N to about 1.7 N.

Example A19. The package of any of Examples A2-A18, wherein the opening crease exhibits a Peak Load of about 1.8 N or less, or more preferably about 1.7 N or less.

Example A20. The package of any of Examples A2-A19, wherein the opening crease exhibits a Peak Load of from about 0.7 N to about 1.8 N or more preferably from about 0.8 N to about 1.7 N.

Example 21. The package of any of the Examples A-A20, wherein the cross-wise crease exhibits a slope of about 2.5 N/mm or less, more preferably about 2.4 N/mm or less or most preferably about 2.3 N/mm or less.

Example A22. The package of any of Examples A-A21, wherein the cross-wise crease exhibits a slope of from about 1.5 N/mm to about 2.5 N/mm, more preferably from about 1.6 N/mm to about 2.4 N/mm or most preferably from about 1.7 N/mm to about 2.3 N/mm.

Example A23. The package of any of Examples A-A22, wherein the opening crease exhibits a slope of about 2.5 N/mm or less, more preferably about 2.4 N/mm or less or most preferably about 2.3 N/mm or less.

Example A24. The package of any of Examples A-A23, wherein the opening crease exhibits a slope of from about 1.5 N/mm to about 2.5 N/mm, more preferably from about 1.6 N/mm to about 2.4 N/mm or most preferably from about 1.7 N/mm to about 2.3 N/mm.

Example A25. The package of any of Examples A-A24, wherein the top fold line comprises a top fold length and where the cross-wise crease comprises a cross-wise crease length, wherein the cross-wise crease length is at least 10 percent of the length of the top fold length, more preferably at least 30 percent the length of the top fold length, and most preferably at least 50 percent the length of the top fold length.

Example A26. The package of Example A25, wherein the cross-wise crease length is from between 10 percent to 100 percent of the top fold length, more preferably from about 30 percent to about 100 percent, or most preferably from about 50 percent to about 100 percent.

Example A27. The package of any of Examples A-A26, wherein the package is recyclable.

Example B. A package of one or more absorbent articles, wherein the one or more absorbent articles are sealed within the package, the package comprising: a plurality of panels, including a consumer-facing panel and a top panel disposed superjacent to the consumer-facing panel, wherein each of the plurality of panels comprises an inner surface and an outer surface; a opening fold line disposed on the top panel, wherein the opening fold line is colinear, at least in part, with an opening crease; wherein the package material comprises natural fibers and wherein the opening crease exhibits a Peak Load of about 1.8 N or less, more preferably about 1.7 N or less.

Example B1. The package of any of Example B, wherein the top panel comprises a front face, an opposing back face, a right face and an opposing left face and an opening tail.

Example B2. The package of any of Examples B-B1, wherein at least one of the front face and/or the back face comprise the opening crease.

Example B3. The package of any of Examples B-B2, wherein the package further comprises a back panel opposed to the consumer-facing panel, a left panel disposed between the consumer-facing panel and the back panel, and a right panel disposed between the consumer-facing panel and the back panel.

Example B4. The package of Example B4 further comprising one or more vertical creases disposed between the consumer-facing panel and the left panel, the consumer-facing panel and the right panel, the right panel and the back panel, and/or the left panel and the back panel.

Example B5. The package of any of Examples B-B4, wherein the opening crease has a depth of greater than about 0.01 mm, more preferably greater than about 0.02 mm, or most preferably greater than about 0.03 mm.

Example B6. The package of any of Examples B-B5, wherein the opening crease has a depth of from about 0.01 mm to about 0.9 mm, more preferably from about 0.02 mm to about 0.7, or most preferably from about 0.03 mm to about 0.5 mm.

Example B7. The package of any of Examples B-B6, wherein the opening crease has a width of from about 0.1 mm to about 7 mm, more preferably from about 0.1 mm to about 5 mm or most preferably from about 0.1 mm to about 4 mm.

Example B8. The package of any of Examples B-B7, wherein the opening crease has a width of from about 0.1 mm to about 3 mm, more preferably from about 0.1 mm to about 2 mm, or most preferably from about 0.1 mm to about 1 mm.

Example B9. The package of any of Examples B-B8, wherein the opening crease is biased from the inner surface toward the outer surface.

Example B10. The package of Example B9, wherein the opening crease is disposed on the front face.

Example B11. The package of any of Examples B-B10, wherein the opening crease exhibits a Peak Load of about 1.8 N or less, or more preferably about 1.7 N or less.

Example B12. The package of any of Examples B-B11, wherein the opening crease exhibits a Peak Load of from about 0.7 N to about 1.8 N or more preferably from about 0.8 N to about 1.7 N.

Example B13. The package of any of Examples B-B12, wherein the opening crease exhibits a slope of about 2.5 N/mm or less, more preferably about 2.4 N/mm or less or most preferably about 2.3 N/mm or less.

Example B14. The package of any of Examples B-B13, wherein the opening crease exhibits a slope of from about 1.5 N/mm to about 2.5 N/mm, more preferably from about 1.6 N/mm to about 2.4 N/mm or most preferably from about 1.7 N/mm to about 2.3 N/mm.

Example B15. The package of any of Examples B-B14, wherein the opening fold line comprises a opening fold length and where the opening crease comprises an opening crease length, wherein the opening crease length is at least 10 percent of the length of the opening fold length, more preferably at least 30 percent the length of the opening fold length, and most preferably at least 50 percent the length of the opening fold length.

Example B16. The package of Example B15, wherein the opening crease length is from between 10 percent to 100 percent of the opening fold length, more preferably from about 30 percent to about 100 percent, or most preferably from about 50 percent to about 100 percent.

Example B17. The package of any of Examples B-B16, wherein a cross-wise crease is disposed between the consumer-facing panel and the top panel.

Example B18. The package of any of Examples B-B17, wherein the package is recyclable.

Example C. A package of one or more absorbent articles, wherein the one or more absorbent articles are sealed within the package, the package comprising: a plurality of panels, including a consumer-facing panel and a top panel disposed superjacent to the consumer-facing panel, wherein each of the plurality of panels comprises an inner surface and an outer surface; a top fold line disposed between the consumer-facing panel and the top panel, wherein the top fold line is colinear, at least in part, with a cross-wise crease; wherein the package material comprises natural fibers and has a basis weight of between 60 gsm to 120 gsm, more preferably between 65 gsm to 105 gsm, or most preferably between 70 gsm to 90 gsm, as determined via ISO 536 as modified herein.

Example C1. The package of Example C, wherein the top panel comprises a front face, an opposing back face, a right face and an opposing left face and an opening tail.

Example C2. The package of Example C1, wherein at least one of the front face or the back face comprise an opening crease.

Example C3. The package of any of Examples C1 or C2, wherein the right face and/or the left face comprise gusset creases.

Example C4. The package of any of the preceding Examples, wherein the package further comprises a back panel opposed to the consumer-facing panel, a left panel disposed between the consumer-facing panel and the back panel, and a right panel disposed between the consumer-facing panel and the back panel.

Example C5. The package of Example C4 further comprising one or more vertical creases disposed between the consumer-facing panel and the left panel, the consumer-facing panel and the right panel, the right panel and the back panel, and/or the left panel and the back panel.

Example C6. The package of any of the preceding Examples, wherein the cross-wise crease is disposed in a first plane and a top edge of the one or more absorbent articles is disposed in a second plane, and wherein a distance between the first plane and the second plane is about 5 mm or less, more preferably about 3 mm or less, or most preferably about 2 mm or less.

Example C7. The package of any of the preceding Examples, wherein the cross-wise crease has a depth of greater than about 0.01 mm, more preferably greater than about 0.02 mm, or most preferably greater than about 0.03 mm.

Example C8. The package of any of the preceding Examples, wherein the cross-wise crease has a depth of from about 0.01 mm to about 0.9 mm, more preferably from about 0.02 mm to about 0.7, or most preferably from about 0.03 mm to about 0.5 mm.

Example C9. The package of any of Examples C2-C8, wherein the opening crease has a depth of greater than about 0.01 mm, more preferably greater than about 0.02 mm, or most preferably greater than about 0.03 mm.

Example C10. The package of any of Examples C2-C9, wherein the opening crease has a depth of from about 0.01 mm to about 0.9 mm, more preferably from about 0.02 mm to about 0.7, or most preferably from about 0.03 mm to about 0.5 mm.

Example C11. The package of any of the preceding Examples, wherein the cross-wise crease has a width of from about 0.1 mm to about 7 mm, more preferably from about 0.1 mm to about 5 mm, or most preferably from about 0.1 mm to about 4 mm.

Example C12. The package of any of the preceding Examples, wherein the cross-wise crease has a width of from about 0.1 mm to about 3 mm, more preferably from about 0.1 mm to about 2 mm, or most preferably from about 0.1 mm to about 1 mm.

Example C13. The package of any of Examples C2-C12, wherein the opening crease has a width of from about 0.1 mm to about 7 mm, more preferably from about 0.1 mm to about 3 5 mm, or most preferably from about 0.1 mm to about 4 mm.

Example C14. The package of any of Examples C2-C13, wherein the opening crease has a width of from about 0.1 mm to about 3 mm, more preferably from about 0.1 mm to about 2 mm, or most preferably from about 0.1 mm to about 1 mm.

Example C15. The package of any of the preceding Examples, wherein the cross-wise crease is biased from the inner surface toward the outer surface.

Example C16. The package of any of Examples C2-C15, wherein the opening crease is biased from the inner surface toward the outer surface.

Example C17. The package of Example C16, wherein the opening crease is disposed on the front face.

Example C18. The package of any of Examples C3-C17, wherein the pair of gusset creases are biased from the outer surface toward the inner surface.

Example C19. The package of any of Examples C4-C18, wherein the top fold line comprises a first portion disposed between the consumer-facing panel and the top panel, a second portion disposed between the right panel and the top panel, a third portion disposed between the back panel and the top panel, and a fourth portion disposed between the left panel and the top panel, and wherein a first corner is disposed between the consumer-facing panel the right panel, a second corner is disposed between the right panel and the back panel, a third corner is disposed between the back panel and the left panel, and a fourth corner is disposed between the left panel and the consumer-facing panel.

Example C20. The package of Example C19, wherein the cross-wise crease comprises a first section disposed between the consumer-facing panel and the top panel, wherein the first section comprises a first part and a second part, the first part extending from the fourth corner toward a vertical centerline of the consumer-facing panel and the second part extending from the first corner toward the centerline of the consumer-facing panel.

Example C21. The package of Example C20, wherein the first part and the second part have a cumulative length which is less than a length of the first portion of the top fold line.

Example C22. The package of Examples C20 and C21, wherein the cumulative length is at least 10 percent of the first portion length, more preferably at least 30 percent of the first portion length, or most preferably at least 50 percent of the first portion length.

Example C23. The package of any of Examples C19-C22, wherein the cross-wise crease is disposed, at least in part between the consumer-facing panel and the top panel, the right and left panels and the top panel, and the back panel and the top panel.

Example C24. The package of any of the preceding Examples, wherein the package material comprises at least 50 percent by weight natural fibers, more preferably at least 70 percent by weight natural fibers, or most preferably at least 90 percent by weight of natural fibers.

Example C25. The package of any of the preceding Examples, wherein the package material comprises between 50 and 100 percent by weight of natural fibers, more preferably between 65 and 99 percent by weight of natural fibers, or most preferably between 75 and 95 percent by weight of natural fibers.

Example C26. The package of any of the preceding Examples, wherein the natural fibers of the packaging material comprise at least one of: cellulose-based fibers, bamboo based fibers, cotton, abaca, kenaf, sabai grass, flax, esparto grass, straw, jute hemp, bagasse, milkweed floss fibers, pineapple leaf fibers, wood fibers, or pulp fibers.

Example C27. The package of any of the preceding Examples, wherein the natural fibers comprise at least one of wood fibers or pulp fibers.

Example C28. The package of any of the preceding Examples, wherein the package material comprises a weight percentage of non-recyclable material of less than about 30 percent by weight, more preferably less than about 20 percent by weight, or most preferably less than about 10 percent by weight.

Example C29. The package of any of the preceding Examples, wherein the package material comprises a weight percentage of non-recyclable material of from between 0.5 percent to about 30 percent, more preferably from about 0.5 percent to about 20 percent, or most preferably from about 0.5 percent to about 10 percent.

Example C30. The package of any of the preceding Examples, wherein the package material comprises a weight percentage of non-recyclable material of less than about 5 percent by weight.

Example C31. The package of any of the preceding Examples, wherein the package material comprises a weight percentage of non-recyclable material of from between 0.5 percent to about 5 percent.

Example C32. The package of any of the preceding Examples, wherein the package material exhibits a recyclable percentage of at least 70 percent, more preferably at least 80 percent, or most preferably at least 90 percent, as determined by PTS-RH:021/97 (Draft October 2019) method.

Example C33. The package of any of the preceding Examples, wherein the package material exhibits an overall "pass" test outcome, as determined via the PTS-RH:021/97 (Draft October 2019) method.
Example C34. The package of any of the preceding Examples, wherein the package material exhibits a recyclable percentage of between, 70 percent to about 99.9 percent, more preferably from about 85 percent to about 99.9 percent, or most preferably from about 90 percent to about 99.9 percent.
Example C35. The package of any of the preceding Examples, wherein the package material comprises recycled natural fibers as determined via visual inspection.
Example C36. The package of any of the preceding Examples, wherein the package material does not comprise a barrier layer.
Example C37. The package of any of Examples C-C35, wherein the package material comprises a barrier layer.
Example C38. The package of any of the preceding Examples, wherein the one or more absorbent articles exhibit an in-bag stack height of less than about 150 mm, more preferably less than about 100 mm, or most preferably less than about 70 mm, in accordance with the in-bag stack height method.
Example C39. The package of any of the preceding Examples, wherein the one or more absorbent articles exhibit an in-bag stack height of from between 70 mm to about 150 mm, more preferably from about 70 mm to about 100 mm, or most preferably from about 70 mm to about 90 mm.
Example C40. The package of any of the preceding Examples, wherein the one or more absorbent articles comprise at least one of diaper pants, incontinence pads, diapers, or adult incontinence briefs.

Test Methods

ASTM F88-06—Seal Tensile Strength

This test method determines the strength of a seal in flexible barrier materials by measuring the force required to separate a test strip of material containing the seal. Seal strength is measured in accordance with compendial method ASTM F0088-06 on a constant rate of extension tensile tester, with procedural specifics noted herein. A suitable instrument is the Instron Model 5965 using Bluehill Universal Software, both available from Instron Norwood, MA), or equivalent. All measurements are performed in a laboratory maintained at 23° C.±2 C.° and 50%±2% relative humidity and test samples are conditioned in this environment for 2 hours prior to testing.

The preparation of the test specimens and test procedure is described in the referenced ASTM method, with the following specific details. The test specimen is cut to a width of 1.0 inch, the grip separation rate is 300 mm/min, and the tail-holding method is unsupported. The maximum force encountered as the test specimen is stressed to failure is recorded as force per unit width to the nearest 0.1 N/in. The test is repeated for a total of five replicate test specimens. Calculate the arithmetic mean for maximum seal strength and report as Tensile Strength to the nearest 0.1 N/in.

ISO 1924-3—Tensile Properties (Tensile Strength, Stretch, Energy Absorption)

The tensile properties (tensile strength, stretch and energy absorption) of a test sample are calculated from measured force and elongation values obtained using a constant rate of elongation test until the sample breaks. The test is run in accordance with compendial method ISO 1924-3, with modifications noted herein. Measurements are made on a constant rate of extension tensile tester using a load cell for which the forces measured are within 1% to 99% of the limit of the cell. A suitable instrument is the MTS Alliance using Test Suite Software, available from MTS Systems Corp., Eden Prairie, MN, or equivalent. All measurements are performed in a laboratory maintained at 23° C.±2 C.° and 50%±2% relative humidity and test samples are conditioned in this environment for at least 2 hours prior to testing.

Measurements are made on both MD (machine direction) and CD (cross direction) test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is cut to a width of 25.4 mm with a length that can accommodate a test span of 50.8 mm. The long side of the sample is parallel to the direction of interest (MD, CD). Normally in finished packages, the MD runs from the bottom to the top of the package, but this can be verified by determining the fiber orientation if in doubt. Ten replicate test samples should be prepared from the MD and ten additional replicates from the CD.

Program the tensile tester for a constant rate of extension uniaxial elongation to break as follows. Set the gauge length (test span) to 50.8 mm using a calibrated gauge block and zero the crosshead. Insert the test sample into the grips such that the long side is centered and parallel to the central pull axis of the tensile tester. Raise the crosshead at a rate of 25.4 mm/min until the test sample breaks, collecting force (N) and extension (mm) data at 100 Hz throughout the test. Construct a graph of force (N) versus extension (mm). Read the maximum force (N) from the graph and record as Peak Force to the nearest 0.1 N, noting MD or CD. Read the extension at the maximum force (N) from the graph and record as Elongation at Break to the nearest 0.01 mm, noting MD or CD. From the graph, determine the point (z) where the tangent to the curve, with a slope equal to the maximum slope of the curve, intersects the elongation axis. Now calculate the area under the force vs elongation curve from point z up to the point of maximum force and report to the nearest 0.1 mJ, noting MD or CD. [Refer to FIG. 2 in ISO 1924-3 for a depiction of a typical force vs elongation curve where point z is denoted.]

Calculate the arithmetic mean Peak Force for all MD replicates and then all CD replicates and record respectively as Mean MD Peak Force and Mean CD Peak Force to the nearest 0.1 N. Calculate the arithmetic mean Elongation at Break for all MD replicates and then all CD replicates and record respectively as Mean MD Elongation at Break and Mean CD Elongation at Break to the nearest 0.01 mm Calculate the arithmetic mean area under the force vs elongation curve for all MD replicates and then all CD replicates and record respectively as Mean Area Under MD Curve and Mean Area Under CD Curve to the nearest 0.1 mJ.

Tensile strength is calculated by dividing the Mean Peak Force (N) by the width of the test sample (25.4 mm). Calculate the tensile strength for the MD replicates and then the CD replicates and report respectively as MD Tensile Strength and CD Tensile Strength to the nearest 0.1 kN/m.

Stretch at break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

ISO 2758—Burst Strength

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23° C.+/−2 C.° and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles, or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

ISO 534—Caliper

The caliper, or thickness, of a single-layer test sample is measured under a static load by a micrometer, in accordance with compendial method ISO 534, with modifications noted herein. All measurements are performed in a laboratory maintained at 23° C.±2 C.° and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm$^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

ISO 536—Basis Weight

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

Crease Dimensions Using CLSM

The width and/or depth of a crease line imparted onto packaging material are measured using a 3D Confocal Laser Scanning Microscope (CLSM) with a resolution of 5 nm. A suitable instrument is the Keyence VK-X1050 (available from Keyence Corporation of America, Itasca, IL, USA), or equivalent. The instrument is calibrated according to the manufacturer's instructions prior to use to ensure an accurate distance scale. Test samples are conditioned at 23° C.±2° C. and 50%±2% relative humidity for 2 hours prior to testing and all testing is performed under these same environmental conditions.

The test specimen is excised from either an intact, finished bag of product or from a test material that has been imparted with crease lines. The test specimen is taken from an area that includes a crease line but is otherwise free of folds, wrinkles or seams. The dimensions of the test specimen are to be decided by the analyst. However, the specimen must be small enough to fit onto the stage of the CLSM, and the entire width of the crease must be centered within the specimen. Care should be used when prepping and handling the test specimen to ensure that the integrity of the crease line and surrounding area are maintained and no distortions of either are imparted.

The test specimen is mounted onto the stage of the CLSM using small pieces of tape (any convenient source) to create an overall flat (non-wavy) surface without distorting the test specimen. The tape is to be placed along the outermost edges of the test specimen while avoiding the crease line and its immediately surrounding area that will be analyzed. Use the light microscopy function and a low magnification setting to select the area of the test specimen that includes the crease line. Start the measurement of the height profile for the selected area using the confocal laser scanning function at a resolution of 5 nm. To note, if the area to be analyzed is too large, individually collected scans can be stitched together later. In the height profile image, use the top view of the scanned area to define cross section view lines (about ten) that run perpendicular to the crease line in order to create several linear height profiles. Analyze one of the height profiles numerically as follows. Using the "flat" areas surrounding the crease line, define and draw a base line to depict the surface height. To note, when defining the base line, ignore any obvious raised or indented artifacts that may occur along, or immediately adjacent to, the crease line itself. Now measure the distance between the base line and the lowest point of indentation of the crease line and record as Crease Depth to the nearest 1 micron. Measure the width of the crease line using the base line to define the start and end reference points of the depression, and record as Crease Width to the nearest 1 micron. In like fashion, measure and record the depth and width for each height profile created by the ten or so cross section view lines previously created, recording each to the nearest 1 micron.

Repeat the entire procedure for five replicate test specimens that represent five separate crease lines. Calculate the arithmetic mean for all of the individually measured crease depths (within each test specimen, across all five test specimens for a total of about 50 values), and report as Crease Depth to the nearest 1 micron. Calculate the arithmetic mean for all of the individually measured crease widths (within each test specimen, across all five test specimens for a total of about 50 values) and report as Crease Width to the nearest 1 micron.

Opening Tail Height and Seam Offset Measurements

The height of the opening tail and seam offset are dimensional measurements made on the intact, finished bag filled with product. The height of the opening tail 265 is the vertical distance between the height of the product inside of the bag and the uppermost edge of the opening tail. Seam offset is measured at the lateral edges of the opening tail 265 at the top of the bag on both the right and left sides of the seal. When the uppermost seal is formed, if the front of the bag is not aligned perfectly with the back of the bag, then an offset will occur. The magnitude of the offset is measured as the distance that the front lateral edge of the bag extends beyond the back lateral edge of the bag (or vice versa) along the lateral edge of the opening tail. These dimensional measurements are made using a calibrated steel metal ruler traceable to NIST, or equivalent. Test samples are conditioned at 23° C.±2° C. and 50%±2% relative humidity for 2 hours prior to testing and all pre-conditioning and testing is performed under these same environmental conditions.

The test sample is the intact, filled bag of product. Prior to testing, a pre-conditioning step is performed on the test samples in an effort to eliminate any compression effects caused by case-packing. To pre-condition the intact, filled bag, first remove it from any outer case packaging that might be present, and then place it onto a flat, rigid surface in its upright position (i.e. base of the bag is facing the rigid surface). Allow the bag to sit freely in its upright position for 72 hours. After 72 hours have elapsed, promptly proceed with the dimensional measurements.

Measure the height of the opening tail as follows. While the test sample is sitting on a flat, rigid surface with the front panel of the bag facing the analyst, measure the distance between the bottom edge of the bag and the uppermost edge of the opening tail using the ruler. Make these measurements on both the left and right sides of the bag and record to the nearest 0.01 cm as Full Bag Height$_{left}$ and Full Bag Height$_{right}$, respectively. The vertical height of the product inside the filled bag is also measured using the ruler and recorded as Product Height to the nearest 0.01 cm. To note, the product height is the distance from the flat, rigid surface to the top edge of the product inside the bag, and it may be necessary to sacrifice a filled bag (i.e. cut open the bag) to make this measurement. Subtract the Product Height from the Full Bag Height$_{left}$ and record as Opening Tail Height$_{left}$ to the nearest 0.01 cm. Subtract the Product Height from the Full Bag Height$_{right}$ and record as Opening Tail Height$_{right}$ to the nearest 0.01 cm. Now calculate the average between Opening Tail Height$_{left}$ and Opening Tail Height$_{right}$ and record as Opening Tail Height to the nearest 0.01 cm.

Measure the seam offset as follows. Locate the opening tail 265 on the top side of the bag. Inspect the left and right lateral edges of the opening tail, both front and back. Use the ruler to measure the distance that the front side of the lateral edge extends beyond the back side of the lateral edge (or vice versa) at the left lateral edge of the seam, and record as Seam Offset$_{left}$ to the nearest 0.1 mm. In like fashion, make the same inspection and measurement at the right lateral edge of the seam and record as Seam Offset$_{right}$ to the nearest 0.1 mm Now calculate the average between Seam Offset$_{left}$ and Seam Offset$_{right}$ and record as Seam Offset to the nearest 0.1 mm.

In like fashion, the entire procedure is repeated for a total of ten replicate test sample bags. The reported value for each of the parameters is the arithmetic mean of the ten individually recorded measurements for Opening Tail Height to the nearest 0.01 cm and Seam Offset to the nearest 0.1 mm Bending Method The bending properties of a sample are measured using an ultra sensitive 3 point bend test on a constant rate of extension tensile tester (a suitable instrument is the MTS Alliance using Testworks 4.0 Software or TestSuite Software, as available from MTS Systems Corp., Eden Prairie, MN) using a load cell for which the forces measured are within 1% to 99% of the limit of the cell. All testing is performed in a room controlled at 23° C.±3° C. and 50%±2% relative humidity.

The ultra sensitive 3 point bend method is designed to maximize the force signal to noise ratio when testing materials with very low bending forces. The force signal is maximized by using a high sensitivity load cell (e.g., 5N), using a small span (load is proportional to the span cubed) and using a wide specimen width (total measured load is directly proportional to width). The fixture is designed such that the bending measurement is performed in tension, allowing the fixture mass to be kept to a minimum. Noise in the force signal is minimized by holding the load cell stationary to reduce mechanical vibration and inertial effect and by making the mass of the fixture attached to the load cell as low as possible.

Figure 14A:
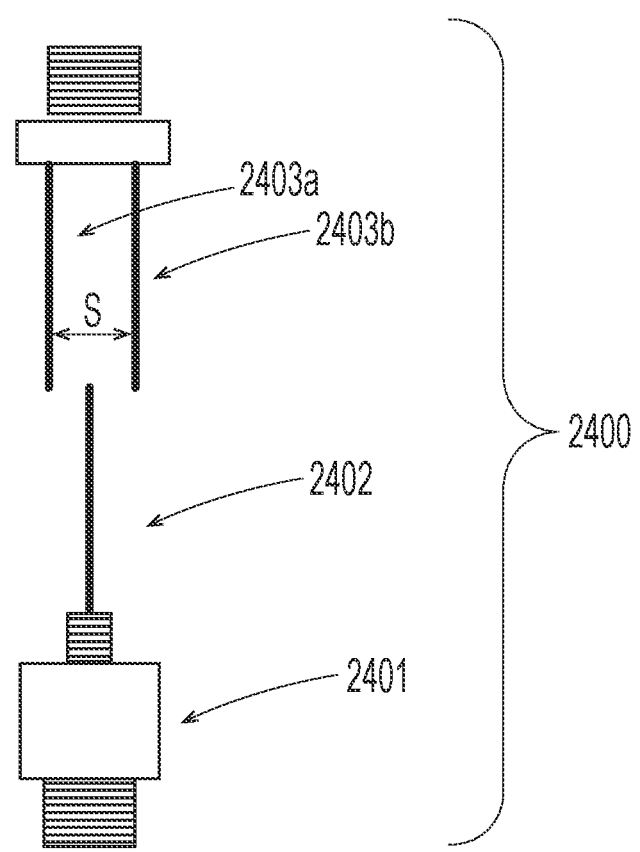
FIGS. 14A-14C are schematic representations showing an ultra sensitive fixture utilized in the Bending Method.
Figure 14B:
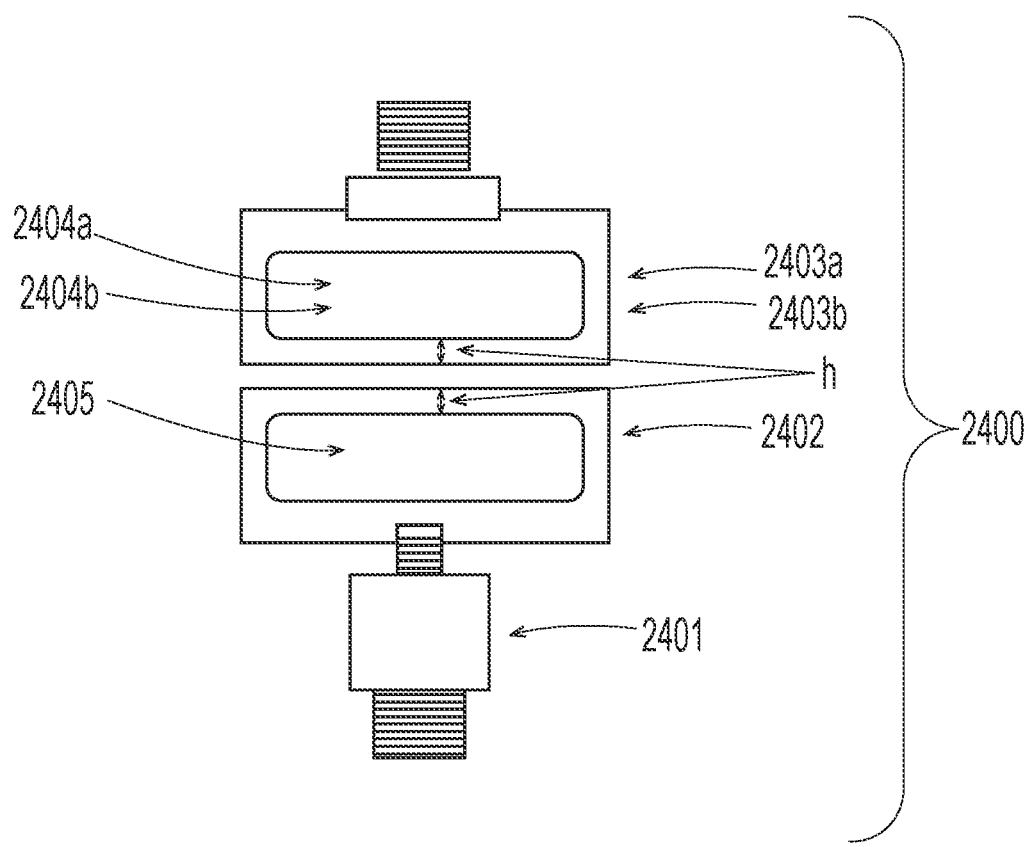
Figure 14C:
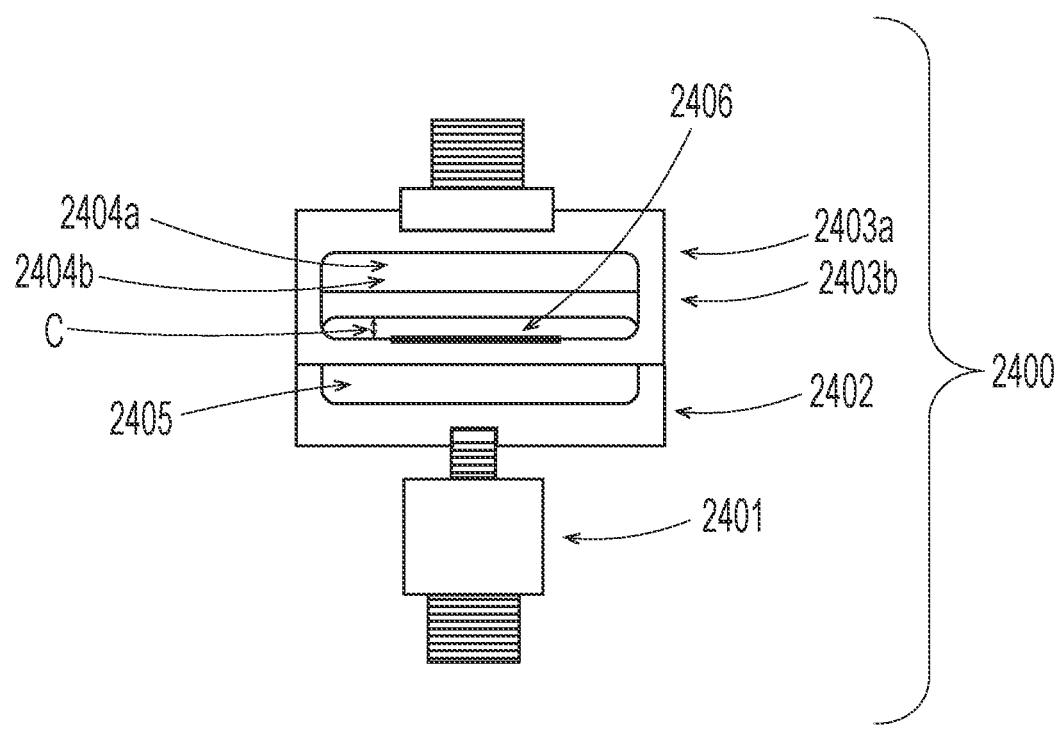

Referring to FIGS. 14A-14C, the load cell 2401 is mounted on the stationary crosshead of the tensile tester. The ultra sensitive fixture 2400 consists of three thin blades constructed of a lightweight, rigid material (such as aluminum, or equivalent). Each blade has a thickness of 1.0 mm, rounded edges and a length that is able to accommodate the bending width of the test specimen. Each of the blades has a cavity 2404a and 2404b (outside blades) and 2405 (central blade) cut out to create a height, h, of 5 mm of blade material along their horizontal edges. The two outside blades 2403a and 2403b are mounted horizontally to the moveable crosshead of the tensile tester, aligned parallel to each other, with their horizontal edges vertically aligned. The span, s, between the two outside blades 2403a and 2403b is 5 mm±0.1 mm (inside edge to inside edge). The central blade 2402 is mounted to the load cell on the stationary crosshead of the tensile tester. When in place, the central blade 2402 is parallel to the two outside blades 2403a and 2403b and centered at the midpoint between the outside blades 2403a and 2403b. The blade fixtures include integral adapters appropriate to fit the respective positions on the tensile tester frame and lock into position such that the horizontal edges of the blades are orthogonal to the motion of the crossbeam of the tensile tester.

Samples are conditioned at 23° C.±3° C. and 50%±2% relative humidity two hours prior to testing. There are two types of specimens prepared for this test: a control specimen and a test specimen. Specimens are excised from either an intact, finished bag of product or from a test material that has been imparted with crease lines. The control specimen is taken from an area of the bag (or sample material) that is free of folds, wrinkles, seams, or crease lines. Additionally, the control specimen is to be cut to the same dimensions as the test specimen, and the long side of the control specimen has the same directional orientation on the bag (or sample material) as the test specimen. The test specimen is taken from an area of the bag (or sample material) that includes a crease line but is otherwise free of additional folds, wrinkles, or seams. The crease line is to be laterally centered along the long side of the test specimen. The dimensions of the test specimen are decided by the analyst, however the width (short side) must be at least 10 mm and the length (which corresponds to the "bending width") should be as long as possible to provide a sufficient load signal. When the sample is sided, a control specimen and test specimen are prepared from each side.

The test is performed in tension. The tensile tester is programmed such that the moveable crosshead is set to move in a direction opposite of the stationary crosshead at a rate of 1.0 mm/sec. Crosshead movement begins with the specimen 2406 lying flat and undeflected on the outer blades 2403a and 2403b, continues with the inner horizontal edge of cavity 2405 in the central blade 2402 coming into contact with the top surface of the specimen 2406, and further continues for an additional 10 mm of crosshead movement. Force (N) and displacement (mm) are collected at 50 Hz throughout.

Prior to loading the specimen 2406, the outside blades 2403a and 2403b are moved towards and then past central blade 2402 until there is approximately a 3 mm clearance, c, between the inner horizontal edges of cavities 2404a and 2404b in the outside blades 2403a and 2403b and the inner horizontal edge of cavity 2405 in the central blade 2402 (see FIG. 14C). The specimen 2406 is placed within clearance C such that it spans the inner horizontal edges of cavities 2404a and 2404b in the outside blades 2403a and 2403b, oriented such that the short side of the specimen is perpendicular to the horizontal edges of the blades. Note which side of the specimen 2406 faces the central blade 2402. Center the specimen 2406 between the outside blades 2403a and 2403b. Slowly move the outside blades 2403a and 2403b in a direction opposite of the stationary crosshead until the inner horizontal edge of cavity 2405 in the central blade 2402 touches the top surface of the specimen 2406.

Force (N) is plotted versus displacement (mm). The maximum peak force is recorded as Peak Load to the nearest 0.001 N. The area under the curve up to the maximum peak force is calculated and recorded as Energy to Peak to the nearest 0.001 N-mm. The slope of the linear portion of the force versus displacement curve is determined and recorded as Slope to the nearest 0.001 N/mm.

In like fashion, repeat the entire test sequence for a total of five control specimens and five test specimens for each side of the sample, if applicable, noting which side faces the central blade 2402 on the stationary crosshead for each replicate for sided samples. The reported value for each of the parameters is the arithmetic mean of the five individually recorded measurements within like specimens (e.g., control and test) for Peak Load to the nearest 0.001 N, Energy to Peak to the nearest 0.001 N-mm, and Slope to the nearest 0.001 N/mm. The results for the control specimen can be directly compared to those for the test specimen, for each respective side of the sample if applicable.

Bag Compression

Bag compression is measured for a finished bag filled with product on a Constant Rate of Extension (CRE) universal mechanical test system (a suitable instrument is the MTS Alliance using TestSuite Software, as available from MTS Systems Corp., Eden Prairie, MN) using a load cell for which the forces measured are within 1% to 99% of the limit of the cell. Both the stationary and movable fixtures are rectangular, stainless steel platens that have dimensions that are larger than the top and bottom surfaces of the filled bag. Both platens have adapters compatible with the mounts of the CRE test machine, capable of securing the platens parallel to each other and orthogonal to the motion of the crossbeam of the CRE test machine. All pre-conditioning and testing is performed in a room controlled at 23° C.±3° C. and 50%±2% relative humidity.

The test sample is the intact, filled bag of products. Prior to testing, a pre-conditioning step is performed on the test samples in an effort to eliminate any compression effects caused by case-packing. During the pre-conditioning step, a clamp is attached to the upper seal of the bag (the "fin") such that the clamp can be hung to enable the bag to be freely suspended under its own weight for 24 hours. To pre-condition the intact, filled bag, first remove it from any outer case packaging that might be present, and then place it onto a flat, rigid surface in its upright position (i.e., base of the bag is facing the rigid surface). Locate the opening tail 265 on the top side of the bag. Determine the length of the opening tail 265 using a calibrated steel metal ruler traceable to NIST, or equivalent, and record as Length of Upper Seal to the nearest 0.1 cm. The vertical height of the product inside the filled bag is also measured using the ruler and recorded as Product Height to the nearest millimeter. To note, the product height is the distance from the flat, rigid surface to the top edge of the product inside the bag, and it may be necessary to sacrifice a filled bag (i.e., cut open the bag) to make this measurement. Using an intact bag, place a clamp such that it grips the opening tail 265 at its lengthwise midpoint, and then hang the clamp such that the bag is suspended under its own weight. Allow the bag to hang freely for 24 hours. After 24 hours have elapsed, remove the clamp and set the intact bag in its upright position on a flat, rigid surface, and promptly proceed with the compression test.

Prepare the CRE test machine for a compression test to measure force and distance. Set a defined distance between the platens that is sufficient to accommodate the height of the test sample bag such that the initial force applied to the bag is zero. Record this distance as Do to the nearest 0.1 mm Zero the crosshead and load cell. Place the test sample bag upright (i.e., base of the bag facing down) onto the bottom platen such that the bag is centered (widthwise and lengthwise) under the upper platen. Lower the crosshead at a rate of 1 mm/s to a platen separation that is equal to 5 mm less than the predetermined Product Height, then raise the crosshead until a load of 0.05 N is reached. Then return the crosshead to the original platen separation (Do). Collect Force (N) versus Distance, D, (mm) data at a rate of 25 Hz.

Construct a graph of force (N) versus height (mm) where height (H) is the distance between platens, calculated by $H=D_0-D$. Note that force and displacement are positive values throughout the test. From the compression portion (downward movement of the upper platen) of the resultant force vs height curve, determine the following parameters. Record the height at a force of 0.2 N as Initial Height to the nearest 0.1 mm Record the height that is 3 mm greater than the predetermined Product Height as Compression Height to the nearest 1 mm Record the force at the Compression Height as Force at Compression Height to the nearest 0.1 N. Divide the Force at Compression Height by the predetermined Length of Upper Seal and record as Normalized Force at Compression Height to the nearest 0.01 N/cm. Calculate the area under the compression portion of the curve up to the Compression Height and record as Energy of Compression to the nearest 0.1 N*mm Now, from the recovery portion (upward movement of the upper platen) of the resultant force vs height curve, determine the following parameters. Record the height at a force of 0.2 N as Final Height to the nearest 0.1 mm Calculate the area under the curve between the Compression Height and the Final Height, and record as Energy of Compression to the nearest 0.01 N*mm.

In like fashion, the entire procedure is repeated for a total of five replicate test samples. The reported value for each of the parameters is the arithmetic mean of the five individually recorded measurements for Normalized Force at Compression Height to the nearest 0.01 N/cm, Energy of Compression to the nearest 0.1 N*mm, and Energy of Recovery to the nearest 0.01 N*mm In-Bag Stack Height Test The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 3). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm Percentage of Colorant Coverage Measurement Method The Percentage of Colorant Coverage measurement method measures the percent area of colorant coverage on a package panel. A flatbed scanner capable of scanning a minimum of 24 bit color at 800 dpi with manual control of color management (a suitable scanner is an Epson Perfection V750 Pro from Epson America Inc., Long Beach CA, or equivalent) is used to acquire images. The scanner is interfaced with a computer running color calibration software capable of calibrating the scanner against a color reflection IT8 target utilizing a corresponding reference file compliant with ANSI method IT8.7/2-1993 (suitable color calibration software is Monaco EZColor or i1Studio available from X-Rite Grand Rapids, MI, or equivalent). The color calibration software constructs an International Color Consortium (ICC) color profile for the scanner, which is used to color correct an output image using an image acquisition program that supports application of ICC profiles. The color corrected image is then segmented via color thresholding using color analysis software (a suitable image color analysis software is MATLAB R2017b available from The Mathworks, Inc., Natick, MA).

The samples are conditioned at about 23° C.±2° C. and about 50%±2% relative humidity for 2 hours prior to testing.

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for a scanner, which will be applied within the image analysis program to correct the color of subsequent output images.

A sample is obtained from a package or package materials with identified panels. A single panel is selected and cut along its perimeter to remove it for testing. Panels selected for testing should not contain tears or wrinkles.

The scanner lid is opened, and the sample carefully laid flat on the center of the scanner glass with the colored surface oriented toward the glass. A scan containing a panel region is acquired at 24 bit color with a resolution of 800 dpi (approximately 31.5 pixels per mm) in reflectance mode. The ICC color profile is assigned to the image producing a color corrected sRGB image. This calibrated image is saved in an uncompressed format to retain the calibrated R,G,B color values, such as a TIFF file, prior to analysis.

The calibrated image is opened in the color analysis software. The image is smoothed using a 2D Gaussian filter with a sigma of 3 to blur out any individual dots of colorant. Next, utilizing a color thresholding program, a color space to perform the color thresholding is selected, for example CIELAB with its three color values L*,a*,b*. Then a region of interest (ROI) boundary is manually drawn within a visibly discernable region of only the base color, without any colorants present, to identify its color space values. A panel with no visible base color region will be deemed to have 100% colorant coverage. The thresholding levels in all three channels of the selected color space are then manually adjusted to segment the regions of the panel that contain colorant coverage from those regions of the base color. The area of the panel containing colorant coverage is measured and the percentage of the area of the panel containing colorant coverage is calculated and recorded to the nearest whole percent.

In like manner, prepare, scan, and analyze six replicate package panels. Calculate and report the arithmetic mean of the measured percent area of colorant coverage values to the nearest whole percent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package of one or more absorbent articles, wherein the one or more absorbent articles are sealed within the package, the package comprising:
    a plurality of panels, including a consumer-facing panel and a top panel disposed superjacent to the consumer-facing panel, wherein each of the plurality of panels comprises an inner surface and an outer surface;
    a top fold line disposed between the consumer-facing panel and the top panel, wherein the top fold line is colinear, at least in part, with a cross-wise crease;
    a package material, wherein the package material comprises natural fibers and has a basis weight of between 60 gsm to 120 gsm, as determined via the Basis Weight Method;
    wherein the cross-wise crease is biased from the inner surface toward the outer surface;
    wherein the cross-wise crease has a depth of from 0.01 mm to 0.9 mm and a width of from 0.1 mm to 7 mm;
    wherein the cross-wise crease is disposed in a first plane and a top edge of the one or more absorbent articles is disposed in a second plane, and wherein a distance between the first plane and the second plane is 5 mm or less;
    wherein the top panel comprises a front face, an opposing back face, a right face and an opposing left face and an opening tail;
    wherein the right face and/or the left face comprise gusset creases; and
    wherein the gusset creases are biased from the outer surface to the inner surface.

2. The package of claim 1, wherein at least one of the front face or the back face comprise an opening crease.

3. The package of claim 2, wherein the opening crease is biased from the inner surface toward the outer surface.

4. The package of claim 3, wherein the opening crease is disposed on the front face.

5. The package of claim 1, wherein the package further comprises a back panel opposed to the consumer-facing panel, a left panel disposed between the consumer-facing panel and the back panel, and a right panel disposed between the consumer-facing panel and the back panel.

6. The package of claim 5 further comprising one or more vertical creases disposed between the consumer-facing panel and the left panel, the consumer-facing panel and the right panel, the right panel and the back panel, and/or the left panel and the back panel.

7. The package of claim 5, wherein the top fold line comprises a first portion disposed between the consumer-facing panel and the top panel, a second portion disposed between the right panel and the top panel, a third portion disposed between the back panel and the top panel, and a fourth portion disposed between the left panel and the top panel, and wherein a first corner is disposed between the consumer-facing panel the right panel, a second corner is disposed between the right panel and the back panel, a third corner is disposed between the back panel and the left panel, and a fourth corner is disposed between the left panel and the consumer-facing panel.

8. The package of claim 7, wherein the cross-wise crease comprises a first section disposed between the consumer-facing panel and the top panel, wherein the first section comprises a first part and a second part, the first part extending from the fourth corner toward a vertical centerline of the consumer-facing panel and the second part extending from the first corner toward the centerline of the consumer-facing panel.

9. The package of claim 8, wherein the first part and the second part have a cumulative length which is less than a length of the first portion of the top fold line.

10. The package of claim 9, wherein the cumulative length is at least 10 percent of the first portion length.

11. The package of any of claim 7, wherein the cross-wise crease is disposed, at least in part between the consumer-facing panel and the top panel, the right and left panels and the top panel, and the back panel and the top panel.

12. The package of claim 1, wherein the cross-wise crease has a width of from 0.1 mm to 3 mm.

13. The package of claim 1, wherein the package material comprises at least 50 percent by weight natural fibers.

14. The package of claim 1, wherein the package material exhibits a recyclable percentage of at least 70 percent as determined by PTS-RH:021/97 (Draft October 2019) method.

15. The package of claim 1, wherein the package material exhibits an overall "pass" test outcome, as determined via the PTS-RH:021/97 (Draft October 2019) method.

16. The package of claim 1, wherein the package material does not comprise a barrier layer.

17. The package of claim 1, wherein the package material comprises a barrier layer.

18. The package of claim 1, wherein the one or more absorbent articles comprise at least one of diaper pants, incontinence pads, diapers, or adult incontinence briefs.

19. The package of claim 1, wherein the cross-wise crease exhibits a Peak Load of from about 0.7 N to about 1.8 N.

\* \* \* \* \*